United States Patent [19]
Timmers et al.

[11] Patent Number: 6,107,421
[45] Date of Patent: Aug. 22, 2000

[54] HETEROCYCLIC METAL COMPLEXES AND OLEFIN POLYMERIZATION PROCESS

[75] Inventors: Francis J. Timmers, Midland; Arthur J. Ashe, III, Chelsea; David D. Devore, Midland; Saleem A. Al-Ahmad, Ypsilanti; Xinggao Fang, Ann Arbor, all of Mich.

[73] Assignees: The Dow Chemical Company, Midland; The Regents of the University of Michigan, Ann Arbor, both of Mich.

[21] Appl. No.: 09/125,180

[22] PCT Filed: Mar. 26, 1997

[86] PCT No.: PCT/US97/04884

§ 371 Date: Aug. 10, 1998

§ 102(e) Date: Aug. 10, 1998

[87] PCT Pub. No.: WO97/35867

PCT Pub. Date: Oct. 2, 1997

Related U.S. Application Data

[60] Provisional application No. 60/014,278, Mar. 27, 1996.

[51] Int. Cl.$^7$ .................................. C08F 4/44; C07F 5/02

[52] U.S. Cl. ..................... 526/134; 526/160; 526/161; 526/172; 526/348.6; 526/943; 556/8; 556/53; 502/104; 502/152; 502/202

[58] Field of Search ..................... 526/134, 133, 526/160, 172, 943, 348.2, 348.4, 340.5, 348.6, 351, 352, 161; 502/117, 155; 556/7, 51, 52, 53, 8

[56] References Cited

U.S. PATENT DOCUMENTS 5,554,775 9/1996 Krishnamurti et al. ................. 556/7

OTHER PUBLICATIONS

Bazan, et al. Aminoboratabenzene Derivatives of Zirconium: A New Class of Olefin Polymerization Catalysts, JACS 1996, 118, 2291–2292, Mar. 1996.

*Primary Examiner*—David W. Wu
*Assistant Examiner*—R. Harlan

[57] ABSTRACT

Metal complexes, addition polymerization catalysts containing the same and olefin polymerization processes using the same comprising a boratabenzene group or divalent derivative thereof are disclosed.

9 Claims, No Drawings

HETEROCYCLIC METAL COMPLEXES AND OLEFIN POLYMERIZATION PROCESS

CROSS-REFERENCE TO RELATED APPLICATION

This application claims benefit of priority from PCT/US97/04884, filed Mar. 26, 1997, and from U.S. Provisional Application, 60/014,278, filed Mar. 27, 1996.

This invention relates to metal complexes and to addition polymerization catalysts formed therefrom that have improved catalytic performance. More particularly the present invention relates to an addition polymerization catalyst composition comprising a Group 3, 4, or Lanthanide metal complex containing a boratabenzene group or divalent derivative thereof bonded via its delocalized π electrons to the metal (also referred to as a boracyclohexadienyl group). In addition, the present invention relates to certain of the foregoing complexes possessing a novel bridged structure. Finally, the invention relates to a method of using the foregoing catalyst compositions in an addition polymerization process for polymerizing addition polymerizable monomers.

In EP-A-416,815 there are disclosed certain constrained geometry metal complexes and catalysts derived by reacting the metal complex with activating cocatalysts. Supported derivatives of such catalysts were prepared by contacting them with a support such as alumina, silica or $MgCl_2$. In U.S. Pat. No. 5,064,802 (EP-A-418,044) there are disclosed certain further catalysts formed by reacting metal complexes with ion forming activating cocatalysts that are salts of Bronsted acids containing a noncoordinating compatible anion. The reference discloses the fact that such complexes are usefully employed as catalysts in addition polymerizations. In EP-A-520,732 an alternative technique for preparing cationic constrained geometry catalysts using borane activators is disclosed.

In U.S. Pat. No. 4,892,851 there are disclosed biscyclopentadienyl Group 4 metal complexes, especially complexes of zirconium or hafnium that are usefully employed with alumoxane activating cocatalysts for use in addition polymerizations, especially the polymerization of aliphatic α-olefins. In a series of patents, W. Spaelick has disclosed certain ring substituted stereorigid bisindenyl complexes and their use as olefin polymerization catalysts. The bridging group of such complexes generically includes silicon, germanium or tin containing divalent groups containing hydride, halogen, $C_{1-10}$ alkyl, $C_{1-10}$ fluoroalkyl, $C_{6-10}$ aryl, $C_{6-10}$ fluoroaryl, $C_{1-10}$ alkoxy, $C_{2-10}$ alkenyl, $C_{7-40}$ aralkyl, $C_{8-40}$ aralkenyl or $C_{7-40}$ alkylaryl groups or ring forming combinations thereof. Such disclosure may be found in U.S. Pat. No. 5,243,001, U.S. Pat. No. 5,145,819, U.S. Pat. No. 5,304,614, U.S. Pat. No. 5,350,817, among others.

Boratabenzenes are anionic ligands which are boron containing six membered ring systems. They are previously known in the art having been described by A. Ashe, et al., *J. Am. Chem. Soc.*, 93, 1804–1805 (1971). They may be prepared by reaction of 1,1-diorgano-1-stannacyclohexa-2,5-diene and a borontrihalide followed by substitution with a hydrocarbyl, amino, silyl or germyl group. Such ligand groups correspond to the formula:

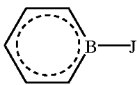

wherein J is selected from the group consisting of hydrogen, hydrocarbyl, dihydrocarbylamino, silyl, germyl, halohydrocarbyl, or halocarbyl, said J having up to 20 non-hydrogen atoms.

It would be desirable if there were provided an improved catalyst system based on the foregoing boratabenzene groups as well as an improved addition polymerization process utilizing such catalyst systems.

As a result of investigations carried out by the present inventors there have now been discovered new and improved Group 3, 4, or Lanthanide metal complexes corresponding to the formula:

or a dimer, solvated adduct, chelated derivative or mixture thereof, wherein:

Y is a divalent derivative of a boratabenzene group or a hydrocarbyl-, dihydrocarbylamino-, silyl- or germyl-substituted boratabenzene group containing up to 50 non-hydrogen atoms that is bonded via its delocalized π-electrons to M;

L is Y or a hydrocarbadiyl group that is bound to M by means of its delocalized π-electrons, or L is a monovalent or divalent amido group, said L group containing up to 50 nonhydrogen atoms;

M is a metal of Group 3, 4 or the Lanthanide series of the Periodic Table of the Elements;

Z is a covalently bound, divalent substituent of up to 50 non-hydrogen atoms having the formula, $-(ER^2{}_2)_m-$, wherein E independently each occurrence is carbon, silicon or germanium, $R^2$ independently each occurrence is selected from the group consisting of hydrocarbyl, hydrocarbyloxy, silyl, and germyl of up to 20 atoms other than hydrogen, and m is an integer from 1 to 3;

X' is a neutral ligand having up to 20 non-hydrogen atoms;

X" independently each occurrence is a monovalent, anionic moiety selected from hydride, halo, hydrocarbyl, silyl, germyl, hydrocarbyloxy, dihydrocarbylamide, siloxy, halohydrocarbyl, halosilyl, silylhydrocarbyl, and dihydrocarbylaminohydrocarbyl having up to 20 non-hydrogen atoms, or two X" groups together form a divalent hydrocarbadiyl group;

n is a number from 0 to 3; and p is an integer from 0 to 2.

According to the present invention there are further provided improved addition polymerization catalyst compositions comprising an activating cocatalyst and one or more Group 3, 4 or Lanthanide metal complexes corresponding to the formula:

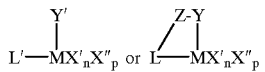

or a dimer, solvated adduct, chelated derivative or mixture thereof, wherein:

Y' is a boratabenzene group or a hydrocarbyl-, dihydrocarbylamino-, silyl- or germyl-substituted boratabenzene group containing up to 50 nonhydrogen atoms that is bonded via its delocalized π-electrons to M;

L' is Y' or a hydrocarbyl group that is bound to M by means of its delocalized π-electrons, or L' is an amido group, said L' group containing up to 50 nonhydrogen atoms;

L and Y are as previously defined;

M is a metal of Group 3, 4 or the Lanthanide series of the Periodic Table of the Elements;

Z is a covalently bound, divalent substituent of up to 50 non-hydrogen atoms having the formula, —(ER$^2_2$)$_m$—, wherein E independently each occurrence is carbon, silicon or germanium, R$^2$ independently each occurrence is selected from the group consisting of hydrocarbyl, hydrocarbyloxy, silyl, and germyl of up to 20 atoms other than hydrogen, and m is an integer from 1 to 3;

X' is a neutral ligand having up to 20 non-hydrogen atoms;

X" independently each occurrence is a monovalent, anionic moiety selected from hydride, halo, hydrocarbyl, silyl, germyl, hydrocarbyloxy, dihydrocarbylamide, siloxy, halohydrocarbyl, halosilyl, silylhydrocarbyl, and dihydrocarbylaminohydrocarbyl having up to 20 non-hydrogen atoms, or two X" groups together form a divalent hydrocarbadiyl group;

n is a number from 0 to 3; and p is an integer from 0 to 2, provided that when two Y groups or two Y' groups are present in the complex, then the activating cocatalyst does not consist solely of an alumoxane.

In a further embodiment there is provided a supported catalyst system comprising one or more of the foregoing metal complexes, one or more activating cocatalysts, and a support material.

Finally there is provided an improved method for polymerization of addition polymerizable monomers using one or more of the above catalyst compositions or catalyst systems. Such addition polymerization processes may be used to prepare polymers for use in making molded articles, films, sheets, foamed materials and in other industrial applications.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups. As used herein, the term "amino" refers to a hydrocarbyl or dihydrocarbyl substituted nitrogen group attached to a nonmetal or to a metalloid. The term "amido" refers to such a hydrocarbyl or dihydrocarbyl group attached to a metal.

Suitable L' groups for use herein include any cyclic, neutral or anionic π-electron containing moiety capable of forming a delocalized bond with the Group 3, 4 or Lanthanide metal. Examples of such neutral groups include arene moieties such as benzene, anthracene or naphthalene, as well as hydrocarbyl-, silyl- or germyl-substituted derivatives of such groups. Examples of anionic π-electron containing moieties include cyclopentadienyl groups, cyclohexadienyl groups, 1,3-pentadienyl groups, and allyl groups, as well as hydrocarbyl-, silyl- or germyl-substituted derivatives of such groups, and partially hydrogenated derivatives of the cyclic groups. In addition, suitable L' groups include the aforementioned boratabenzene or substituted boratabenzene groups represented by Y'. In complexes involving divalent derivatives of such groups, e.g. L or Y groups, it is understood that another atom of the complex is also bonded to such cyclic group thereby forming a bridged system.

By the term "derivative" when used to describe the above cyclic substituted, delocalized π-bonded groups is meant that each atom in the delocalized π-bonded group may independently be substituted with a radical selected from the group consisting of hydrocarbyl radicals, halo-, cyano or dialkylamino- substituted-hydrocarbyl radicals, and hydrocarbyl-substituted metalloid radicals wherein the metalloid is selected from Group 14 of the Periodic Table of the Elements. Suitable hydrocarbyl and substituted-hydrocarbyl radicals used to form derivatives of the substituted, delocalized π-bonded group will contain from 1 to 20 carbon atoms and include straight and branched alkyl radicals, cycloalkyl radicals, aryl radicals, alkyl-substituted cycloalkyl radicals, and alkyl-substituted aromatic radicals. In addition two or more such radicals may together form a fused ring system which may be saturated or unsaturated. Examples of the latter are indenyl-, tetrahydroindenyl-, fluorenyl-, and octahydrofluorenyl- groups, as well as multicyclic, fused ring, boratabenzene derivatives. Suitable hydrocarbyl-substituted organometalloid radicals include mono-, di- and trisubstituted organometalloid radicals of Group 14 elements wherein each of the hydrocarbyl groups contains from 1 to 20 carbon atoms. More particularly, suitable hydrocarbyl-substituted organometalloid radicals include trimethylsilyl, triethylsilyl, ethyldimethylsilyl, methyldiethylsilyl, triphenylgermyl, trimethylgermyl and the like.

Preferred L groups are Y, divalent hydrocarbyl substituted amido groups such as a t-butylamido group, and cyclic, hydrocarbadiyl groups. Examples of the latter include divalent derivatives of cyclopentadienyl, indenyl, fluorenyl, tetrahydroindenyl, tetrahydrofluorenyl, octahydrofluorenyl, cyclohexadienyl, dihydroanthracenyl, hexahydroanthracenyl, and decahydroanthracenyl groups, and C$_{1-10}$ hydrocarbyl-substituted derivatives thereof. Most preferred L groups are divalent derivatives of tetramethylcyclopentadienyl, 2-methylindenyl, 3-methylindenyl, 2,3-dimethylindenyl, 2, 3, 5, 6-tetramethylindenyl, and 2, 3, 5, 6, 7-pentamethylindenyl.

Preferred Z groups are 1,2-ethanediyl, dimethylsilanediyl, diphenylsilanediyl, methylisopropoxysilanediyl, and methylphenylsilanediyl.

Preferred Y' groups correspond to the formula:

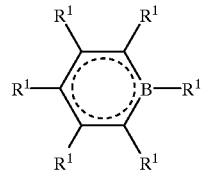

wherein R$^1$ independently each occurrence is hydrogen, hydrocarbyl, dihydrocarbylamino, disilylamino, hydrocarbylsilylamino, halohydrocarbyl, halocarbyl, silyl, germyl, or mixtures thereof, said R$^1$ having up to 50, preferably up to 20 non-hydrogen atoms, and optionally two such R$^1$ groups may be joined together thereby forming a fused ring derivative, and further optionally two such Y' groups may be joined together in a multiple ring system. In complexes involving divalent derivatives of such Y' groups, one R$^1$ is a covalent bond or a divalent derivative of one of the foregoing substituent groups, said R$^1$ being also bonded to another atom of the complex thereby forming a bridged system.

More preferred Y' groups are 1-phenyl-, 1-(N,N-di-(C$_{1-8}$)alkyl)amino, 1-benzyl-, and 1-methyl- substituted boratabenzene groups. Preferred Y groups are divalent derivatives of the foregoing Y' groups. Highly preferably, the divalent derivative of the boratabenzene ligand is substituted with a $C_{1-10}$ hydrocarbyl group in the ring position that is meta to the bridgehead. The skilled artisan will appreciate that the various L and Y ligand groups may be connected at any position of the boratabenzene ring, thereby forming various isomeric products. Mixtures of such isomers may also be utilized.

Examples of highly preferred complexes according to the present invention correspond to the formula:

I wherein:

M is titanium, zirconium or hafnium, preferably zirconium, in the +2, +3, or +4 formal oxidation state;

Z is a covalently bound, divalent substituent of up to 50 non-hydrogen atoms having the formula, $-(ER^2_2)_m-$, wherein E independently each occurrence is carbon, silicon or germanium, $R^2$ independently each occurrence is selected from the group consisting of hydrocarbyl, hydrocarbyloxy, silyl, and germyl of up to 20 atoms other than hydrogen, and m is an integer from 1 to 3;

Y in each occurrence, independently is a divalent derivative of a boratabenzene group or a hydrocarbyl-, dihydrocarbylamino-, silyl- or germyl-substituted boratabenzene group containing up to 50 nonhydrogen atoms that is bonded via its delocalized π-electrons to M;

X' is a conjugated diene having from 4 to 30 non-hydrogen atoms, which forms a π-complex with M when M is in the +2 formal oxidation state, whereupon n is 1 and p is 0; and X" each occurrence is an anionic ligand group that is covalently bonded to M when M is in the +3 or +4 formal oxidation state, whereupon n is 0 and p is 1 or 2, and optionally two X" groups together form a divalent anionic ligand group.

Examples of suitable X' moieties include: $\eta^4$-1,4-diphenyl-1,3-butadiene; $\eta^4$-1,3-pentadiene; $\eta^4$-1-phenyl-1,3-pentadiene; $\eta^4$-1,4-dibenzyl-1,3-butadiene; $\eta^4$-2,4-hexadiene; $\eta^4$-3-methyl-1,3-pentadiene; $\eta^4$-1,4-ditolyl-1,3-butadiene; and $\eta^4$-1,4-bis(trimethylsilyl)-1,3-butadiene. Of the foregoing 1,4-diphenyl-1,3-butadiene, 1-phenyl-1,3-pentadiene, and 2,4 hexadiene are preferred.

Examples of suitable X" moieties include chloride, methyl, benzyl, phenyl, tolyl, t-butyl, methoxide, and trimethylsilyl or two X" groups together are 1,4-butanediyl, s-cis(1,3-butadiene), or s-cis(2,3-dimethyl-1,3-butadiene).

Preferred Z groups are those wherein E is carbon and m is 2 or where E is silicon and m is 1. Also preferably $R^2$ is methyl, phenyl, methoxide, ethoxide, propoxide or butoxide.

In the most preferred embodiment -Y-Z-Y- conforms to one of the following formulas:

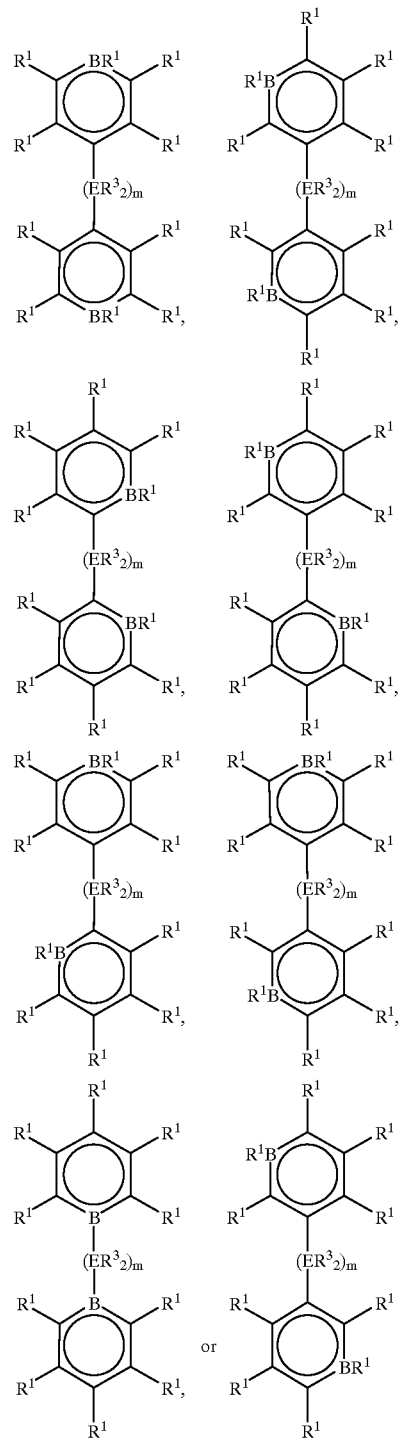

Wherein:

$R^1$ independently each occurrence is hydrogen, hydrocarbyl, dihydrocarbylamino, perfluorohydrocarbyl, silyl substituted hydrocarbyl, or hydrocarbyl substituted silyl of up to 20 nonhydrogen atoms, and optionally two adjacent $R^1$ groups together form a divalent derivative, thereby forming a multicyclic, fused, divalent derivative of a boratabenzene ring system; and $R^2$ is as previously defined.

Most preferably $R^1$ independently each occurrence is hydrogen, $C_{6-20}$ aryl, secondary or tertiary $C_{3-10}$ alkyl, or di-$C_{1-6}$ alkylamino, and $R^2$ independently each occurrence is $C_{1-4}$ alkyl or alkoxy.

In the foregoing structures a negative charge is delocalized on each boratabenzene ring. Both meso and racemic isomers of the metal complexes are obtainable.

Illustrative derivatives of Group 3, 4 or Lanthanide metals of the foregoing formula that may be employed in the practice of the present invention include:

[bis($\eta^6$-1-phenylboratabenzene-4-yl)dimethylsilane] zirconium (II)1,4-diphenyl-1,3-butadiene,

[bis $\eta^6$-1-methyl-2-phenylboratabenzene-4-yl) dimethylsilane]zirconium (II) 1,4-diphenyl-1,3-butadiene,

[bis($\eta^6$-1-phenyl-2-methylboratabenzene-4-yl) dimethylsilane]zirconium (II) 1,4-diphenyl-1,3-butadiene,

[bis($\eta^6$-1-phenylboratabenzene-4-yl)dimethylsilane] titanium (II)1,3-pentadiene,

[bis($\eta^6$-1-methylboratabenzene-4-yl)dimethylsilane] titanium (II) 2-(N,N-dimethylamino)benzyl,

[bis($\eta^6$-1-phenylboratabenzene-4-yl)dimethylsilane] zirconium (IV) dimethyl,

[bis($\eta^6$-1-methyl-2-phenylboratabenzene-4-yl) dimethylsilane]zirconium (IV) dimethyl,

[bis($\eta^6$-1-phenylboratabenzene-4-yl)dimethylsilane] zirconium (IV) dibenzyl,

[bis($\eta^6$-1-phenylboratabenzene-4-yl)dimethylsilane] zirconium (IV) dichloride,

[bis($\eta^6$-1-methylboratabenzene-4-yl)dimethylsilane] zirconium (IV) dimethyl,

[1,2-bis($\eta^6$-1-methyl-2-phenylboratabenzene-4-yl)ethane] zirconium (IV) dibenzyl,

[bis($\eta^6$-1-phenylboratabenzene-4-yl)dimethylsilane] zirconium (IV) dichloride,

[1($\eta^6$-1-phenylboratabenzene-2-yl)-2-($\eta^6$-1-phenylboratabenzene-3-yl)-ethane]zirconium (II)1,4-diphenyl-1,3-butadiene,

[bis($\eta^6$-1-methylboratabenzene-3-yl)dimethylsilane] zirconium (II)1,3-pentadiene,

[($\eta^6$-1-phenylboratabenzene-3-yl) ($\eta^6$-1-phenylboratabenzene-4-yl)dimethylsilane]titanium (III) 2-(N,N-dimethylamino)benzyl,

[($\eta^6$-1-phenylboratabenzene-3-yl) ($\eta^6$-1-phenylboratabenzene-4-yl)dimethylsilane]zirconium (IV) dimethyl,

[($\eta^6$-1-phenylboratabenzene-2-yl) ($\eta^6$-1-phenylboratabenzene-4-yl)dimethylsilane]zirconium (IV) dibenzyl,

[($\eta^6$-1-phenylboratabenzene-2-yl) ($\eta^6$-1-phenylboratabenzene-4-yl)dimethylsilane]zirconium (IV) dichloride,

[bis($\eta^6$-1-phenylboratabenzene-3-yl)dimethylsilane] zirconium (IV) dimethyl,

[($\eta^6$-1-phenylboratabenzene-2-yl) ($\eta^6$-1-phenylboratabenzene-3-yl)dimethylsilane]zirconium (IV) dibenzyl,

[($\eta^6$-1-methylboratabenzene-2-yl) ($\eta^6$-1-phenylboratabenzene-4-yl)dimethylsilane]zirconium (IV) dichloride,

[bis($\eta^6$-1-(N,N-dimethylamino)boratabenzene-4-yl) dimethylsilane]zirconium (II)1,4-diphenyl-1,3-butadiene,

[bis($\eta^6$-1-(N,N-dimethylamino)boratabenzene-4-yl) dimethylsilane]titanium (II) 1,3-pentadiene,

[bis($\eta^6$-1-(N,N-dimethylamino)boratabenzene-4-yl) dimethylsilane]titanium (III) 2-(N,N-dimethylamino) benzyl,

[bis($\eta^6$-1-(N,N-dimethylamino)boratabenzene-4-yl) dimethylsilane]zirconium (IV) dimethyl,

[bis($\eta^6$-1-(N,N-dimethylamino)boratabenzene-4-yl) dimethylsilane]zirconium (IV) dibenzyl,

[bis($\eta^6$-1-(N,N-dimethylamino)boratabenzene-4-yl) dimethylsilane]zirconium (IV) dichloride,

[bis($\eta^6$-1-(N,N-dimethylamino)boratabenzene-4-yl) dimethylsilane]zirconium (IV) dimethyl,

[bis ($\eta^6$-1-(N,N-dimethylamino)boratabenzene-4-yl) dimethylsilane]zirconium (IV) dibenzyl,

[bis($\eta^6$-1-(N,N-dimethylamino)boratabenzene-4-yl) dimethylsilane]zirconium (IV) dichloride,

[1($\eta^6$-1-(N, N-dimethylamino)boratabenzene-2-yl)-2-($\eta^6$-1-(N,N-dimethylamino)-boratabenzene-3-yl)ethane] zirconium (II)1,4-diphenyl-1,3-butadiene,

[bis($\eta^6$-1-(N,N-dimethylamino)boratabenzene-3-yl) dimethylsilane]zirconium (II) 1,3-pentadiene,

[($\eta^6$-1-(N,N-dimethylamino)boratabenzene-3-yl)($\eta^6$-1-(N, N-dimethylamino)-boratabenzene-4-yl)dimethylsilane] titanium (III) 2-(N,N-dimethylamino)benzyl,

[($\eta^6$-1-(N,N-dimethylamino)boratabenzene-3-yl) ($\eta^6$-1-(N, N-dimethylamino)-boratabenzene-4-yl)dimethylsilane] zirconium (IV) dimethyl,

[($\eta^6$-1-(N,N-dimethylamino)boratabenzene-2-yl) ($\eta^6$-1-(N, N-dimethylamino)-boratabenzene-4-yl)dimethylsilane] zirconium (IV) dibenzyl,

[($\eta^6$-1-(N,N-dimethylamino)boratabenzene-2-yl) ($\eta^6$-1-(N, N-dimethylamino)-boratabenzene-4-yl)dimethylsilane] zirconium (IV) dichloride,

[bis($\eta^6$-1-(N,N-dimethylamino)boratabenzene-3-yl) dimethylsilane]zirconium (IV) dimethyl,

[($\eta^6$-1-(N,N-dimethylamino)boratabenzene-2-yl) ($\eta^6$-1-(N, N-dimethylamino)-boratabenzene-4-yl)dimethylsilane] zirconium (IV) dibenzyl,

[1($\eta^6$-1-(N,N-dimethylamino)boratabenzene-2-yl)-2-($\eta^6$-1-(N,N-dimethylamino)-boratabenzene-4-yl)ethane] hafnium (IV) dichloride,

[($\eta^6$-1-(N,N-diisopropylamino)boratabenzene-3-yl) ($\eta^6$-1-(N,N-dimethylamino)-boratabenzene-4-yl) dimethylsilane]zirconium (IV) dimethyl,

[($\eta^6$-1-(N,N-diisopropylamino)boratabenzene-2-yl) ($\eta^6$-1-(N,N-dimethylamino)-boratabenzene-4-yl) dimethylsilane]zirconium (IV) dibenzyl,

[($\eta^6$-1-(N,N-diisopropylamino)boratabenzene-2-yl) ($\eta^6$-1-(N,N-dimethylamino)-boratabenzene-4-yl) dimethylsilane]zirconium (IV) dichloride,

[bis($\eta^6$-1-(N,N-diisopropylamino)boratabenzene-3-yl) dimethylsilane]zirconium (IV) dimethyl,

[($\eta^6$-1-(N,N-diisopropylamino)boratabenzene-2-yl) ($\eta^6$-1-(N,N-dimethylamino)-boratabenzene-4-yl) dimethylsilane]zirconium (IV) dibenzyl,

[1-($\eta^6$-1-(N,N-diisopropylamino)boratabenzene-2-yl)-2-($\eta^6$-1-(N,N-dimethylamino)-boratabenzene-4-yl)ethane] hafnium (IV) dichloride,

[1,2-bis($\eta^6$-1-(N,N-dimethylamino)boratabenzene-4-yl) ethane]zirconium (IV) dimethyl,

[1,2-bis($\eta^6$-1-(N,N-dimethylamino)boratabenzene-4-yl) ethane]zirconium (IV) dibenzyl,

[1,2-bis($\eta^6$-1-(N,N-dimethylamino)boratabenzene-4-yl) ethane]zirconium (IV) dichloride,

[1,2-bis($\eta^6$-1-(N,N-diisopropylamino)boratabenzene-4-yl) ethane]zirconium (IV) dimethyl,

[1,2-bis($\eta^6$-1-(N,N-diisopropylamino)boratabenzene-4-yl) ethane]zirconium (IV) dibenzyl,

[1,2-bis($\eta^6$-1-(N,N-diisopropylamino)boratabenzene-4-yl) ethane]zirconium (IV) dichloride,

[2,2-bis($\eta^6$-1-(N,N-dimethylamino)boratabenzene-4-yl) propane]zirconium (IV) dimethyl,

[2,2-bis($\eta^6$-1-(N,N-dimethylamino)boratabenzene-4-yl)propane]zirconium (IV) dibenzyl,
[2,2-bis($\eta^6$-1-(N,N-dimethylamino)boratabenzene-4-yl)propane]zirconium (IV) dichloride,
[2,2-bis($\eta^6$-1-(N,N-diisopropylamino)boratabenzene-4-yl)propane]zirconium (IV) dimethyl,
[2,2-bis($\eta^6$-1-(N,N-diisopropylamino)boratabenzene-4-yl)propane]zirconium (IV) dibenzyl,
[2,2-bis($\eta^6$-1-(N,N-diisopropylamino)boratabenzene-4-yl)propane]zirconium (IV) dichloride,
[1-($\eta^6$-boratabenzene-2-yl)-2-($\eta^6$-boratabenzene-3-yl)ethane]zirconium (II)1,4-diphenyl-1,3-butadiene,
[bis($\eta^6$-boratabenzene-3-yl)dimethylsilane]zirconium (II)1,3-pentadiene,
[($\eta^6$-boratabenzene-3-yl) ($\eta^6$-boratabenzene-4-yl)dimethylsilane]titanium (III) 2-(N,N-dimethylamino)benzyl,
[($\eta^6$-boratabenzene-3-yl) ($\eta^6$--boratabenzene-4-yl)dimethylsilane]zirconium (IV) dimethyl,
[($\eta^6$-boratabenzene-2-yl) ($\eta^6$-boratabenzene-4-yl)dimethylsilane]zirconium (IV) dibenzyl,
[($\eta^6$-boratabenzene-2-yl) ($\eta^6$-boratabenzene-4-yl)dimethylsilane]zirconium (IV) dichloride,
[bis($\eta^6$-boratabenzene-3-yl)dimethylsilane]zirconium (IV) dimethyl,
[($\eta^6$-boratabenzene-2-yl) ($\eta^6$-boratabenzene-4-yl)dimethylsilane]zirconium (IV) dibenzyl,
[($\eta^6$-boratabenzene-2-yl)-2-($\eta^6$-boratabenzene-4-yl)ethane]hafnium (IV) dichloride
[1,2-bis($\eta^6$-boratabenzene-4-yl)ethane]zironium (IV) dimethyl,
[1,2-bis($\eta^6$-boratabenzene-4-yl)ethane]zirconium (IV) dibenzyl,
[1,2-bis($\eta^6$-boratabenzene-4-yl)ethane]zirconium (IV) dichloride,
[1,2-bis ($\eta^6$-boratabenzene-4-yl)ethane]zirconium (IV) dimethyl,
[1,2-bis($\eta^6$-boratabenzene-4-yl)ethane]zirconium (IV) dibenzyl,
[1,2-bis($\eta^6$-boratabenzene-4-yl)ethane]zirconium (IV) dichloride,
[1,2-bis($\eta^6$-boratabenzene-1-yl)ethane]zirconium (IV) dimethyl,
[1,2-bis($\eta^6$-boratabenzene-1-yl)ethane]zirconium (IV) dibenzyl,
[1,2-bis($\eta^6$-boratabenzene-1-yl)ethane]zirconium (IV) dichloride,
[1,2-bis($\eta^6$-boratabenzene-1-yl)ethane]zirconium (IV) dimethyl,
[1,2-bis($\eta^6$-boratabenzene-1-yl)ethane]zirconium (IV) dibenzyl,
[1,2-bis($\eta^6$-boratabenzene-1-yl)ethane]zirconium (IV) dichloride,
[2,2-bis($\eta^6$-boratabenzene-4-yl)propane]zirconium (IV) dimethyl,
[2,2-bis($\eta^6$-boratabenzene-4-yl)propane]zirconium (IV) dibenzyl,
[2,2-bis($\eta^6$-boratabenzene-4-yl)propane]zirconium (IV) dichloride,
[2,2-bis($\eta^6$-boratabenzene-4-yl)propane]zirconium (IV) dimethyl,
[2,2-bis($\eta^6$-boratabenzene-4-yl)propane]zirconium (IV) dibenzyl,
[2,2-bis($\eta^6$-boratabenzene-4-yl)propane]zirconium (IV) dichloride,
[2,2-bis($\eta^6$-boratabenzene-1-yl)propane]zirconium (IV) dimethyl,
[2,2-bis($\eta^6$-boratabenzene-1-yl)propane]zirconium (IV) dibenzyl,
[2,2-bis($\eta^6$-boratabenzene-1-yl)propane]zirconium (IV) dichloride,
[2,2-bis($\eta^6$-boratabenzene-1-yl)propane]zirconium (IV) dimethyl,
[2,2-bis($\eta^6$-boratabenzene-1-yl)propane]zirconium (IV) dibenzyl,
[2,2-bis($\eta^6$-boratabenzene-1-yl)propane]zirconium (IV) dichloride,
[1,2-bis($\eta^6$-boratabenzene-1-yl)ethane]hafnium (IV) dichloride, and
[2,2-bis($\eta^6$-boratabenzene-1-yl)propane]hafnium (IV) dichloride.

Further examples of preferred complexes according to the present invention correspond to the formula:

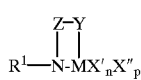

II wherein:

M is titanium, zirconium or hafnium, preferably titanium, in the +2, +3 or +4 formal oxidation state;

Z is a covalently bound, divalent substituent of up to 50 non-hydrogen atoms having the formula, —$(ER^2{}_2)_m$—, wherein E independently each occurrence is carbon, silicon or germanium, $R^2$ independently each occurrence is selected from the group consisting of hydrocarbyl, hydrocarbyloxy, silyl, and germyl of up to 20 atoms other than hydrogen, and m is an integer from 1 to 3;

Y is a divalent derivative of a boratabenzene group or a hydrocarbyl-, dihydrocarbylamino-, silyl- or germyl-substituted boratabenzene group containing up to 50 non-hydrogen atoms that is bonded via its delocalized 7-electrons to M;

$R^1$ is a $C_{1-20}$ hydrocarbyl group,

X' is a conjugated diene having from 4 to 30 non-hydrogen atoms, which forms a π-complex with M when M is in the +2 formal oxidation state, whereupon n is 1 and p is 0; and X" each occurrence is an anionic ligand group that is covalently bonded to M when M is in the +3 or +4 formal oxidation state, whereupon n is 0 and p is 1 or 2, and optionally two X" groups together form a divalent anionic ligand group.

Examples of suitable X' moieties include: 72 $^4$-4-diphenyl-1,3-butadiene; $\eta^4$-1,3-pentadiene; $\eta^4$-1-phenyl-1,3-pentadiene; $\eta^4$-1,4-dibenzyl-1,3-butadiene; $\eta^4$-2,4-hexadiene; $\eta^4$-3-methyl-1,3-pentadiene; $\eta^4$-1,4-ditolyl-1,3-butadiene; and $\eta^4$-1,4-bis(trimethylsilyl)-1,3-butadiene. Of the foregoing 1,4-diphenyl-1,3-butadiene, 1-phenyl-1,3-pentadiene, and 2,4 hexadiene are preferred.

Examples of suitable X" moieties include chloride, methyl, benzyl, phenyl, tolyl, t-butyl, methoxide, and trimethylsilyl or two X" groups together are 1,4-butanediyl, s-cis(1,3-butadiene), or s-cis(2,3-dimethyl-1,3-butadiene).

Preferred Z groups are those wherein E is carbon and m is 2 or E is silicon and m is 1. In addition $R^2$ is methyl, phenyl, methoxide, ethoxide, propoxide or butoxide.

In the most preferred embodiment -Z-Y- is dimethyl($\eta^6$-1-phenylboratabenzene-4-yl)silyl, dimethyl($\eta^6$-1-N,N-dimethylaminoboratabenzene-4-yl)silyl, 1-($\eta^6$-1-phenylboratabenzene-4-yl)ethane-2-yl, or 1-($\eta^6$-1-N,N-dimethylamino)boratabenzene-4-yl)ethane-2-yl.

Examples of the foregoing metal complexes include:

[(t-butylamido)dimethyl(1-phenylboratabenzene-2-yl) silane]titanium dimethyl;
[(t-butylamido)dimethyl(1-phenylboratabenzene-3-yl) silane]titanium dimethyl;
[(t-butylamido)dimethyl(1-phenylboratabenzene-4-yl) silane]titanium dimethyl;
[(t-butylamido)dimethyl (1-N,N-dimethylaminoboratabenzene-2-yl)silane]titanium dimethyl;
[(t-butylamido)dimethyl(1-N,N-dimethylaminoboratabenzene-2-yl)silane]titanium dichloride;
[(t-butylamido)dimethyl (1-N,N-dimethylaminoboratabenzene-4-yl)silane]titanium(II) 1,4-diphenyl-1,3-butadiene;
[1 -(t-butylamido)-2-(1-phenylboratabenzene-2-yl)ethane] titanium dimethyl,
[(t-butylamido)dimethyl(boratabenzene-2-yl)silane] titanium dimethyl;
[(t-butylamido)dimethyl(boratabenzene-3-yl)silane] titanium dimethyl;
[(t-butylamido)dimethyl(boratabenzene-4-yl)silane] titanium dimethyl;
[(t-butylamido)dimethyl(boratabenzene-4-yl)silane] titanium dibenzyl;
[(t-butylamido)dimethyl(boratabenzene-2-yl)silane] titanium dichloride;
[(t-butylamido)dimethyl(boratabenzene-4-yl)silane] titanium(II) 1,4-diphenyl-1,3-butadiene;
[1-(t-butylamido)-2-(boratabenzene-2-yl)ethane]titanium dimethyl
[(cyclohexylamido)dimethyl(1-phenyl)oratabenzene-2-yl) silane]titanium dimethyl;
[(cyclohexylamido)dimethyl(1-pheny)boratabenzene-3-yl) silane]titanium dimethyl;
[(cyclohexylamido)dimethyl(1-phenylboratabenzene-4-yl) silane]titanium dimethyl;
[(cyclohexylamido)dimethyl(1-N,N-dimethylaminoboratabenzene-2-yl)silane]titanium dimethyl;
[(cyclohexylamido)dimethyl(1-N,N-dimethylaminoboratabenzene-2-yl)silane]titanium dichloride;
[(cyclohexylamido)dimethyl(1-N,N-dimethylaminoboratabenzene-4-yl)silane]titanium(II) 1,4-diphenyl-1,3-butadiene;
[1-(cyclohexylamido)-2-(1-phenylboratabenzene-2-yl) ethane]titanium dimethyl,
(cyclohexylamido)dimethyl(boratabenzene-2-yl) silanetitanium dimethyl;
(cyclohexylamido)dimethyl(boratabenzene-3-yl) silanetitanium dimethyl;
(cyclohexylamido)dimethyl(boratabenzene-4-yl) silanetitanium dimethyl;
(cyclohexylamido)dimethyl(boratabenzene-4-yl) silanetitanium dibenzyl;
(cyclohexylamido)dimethyl(boratabenzene-2-yl) silanetitanium dichloride;
(cyclohexylamido)dimethyl(boratabenzene-4-yl) silanetitanium(II) 1,4-diphenyl-1,3-butadiene; and
1(cyclohexylamido)-2-(boratabenzene-2-yl)ethanetitanium dimethyl Still further examples of complexes according to the present invention correspond to the formula:

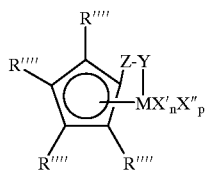

wherein:
M is titanium, zirconium or hafnium, preferably zirconium, in the +2, or +4 formal oxidation state;
Z is a covalently bound, divalent substituent of up to 50 non-hydrogen atoms having the formula, —(ER$^2$$_2$)$_m$—, wherein E independently each occurrence is carbon, silicon or germanium, R$^2$ independently each occurrence is selected from the group consisting of hydrocarbyl, hydrocarbyloxy, silyl, and germyl of up to 20 atoms other than hydrogen, and m is an integer from 1 to 3;
Y is a divalent derivative of a boratabenzene group or a hydrocarbyl-, dihydrocarbylamino-, silyl- or germyl-substituted boratabenzene group containing up to 50 non-hydrogen atoms that is bonded via its delocalized π-electrons to M;
X' is a conjugated diene having from 4 to 30 non-hydrogen atoms, which forms a π-complex with M when M is in the +2 formal oxidation state, whereupon n is 1 and p is 0;
X" each occurrence is an anionic ligand group that is covalently bonded to M when M is in the +4 formal oxidation state, whereupon n is 0 and p is 2, and optionally two X" groups together form a divalent anionic ligand group; and
R"" is hydrogen, hydrocarbyl, silyl, halo-, cyano, dialkylamino, halohydrocarbyl, halocarbyl, dialkylamino substituted-hydrocarbyl, or hydrocarbyl-substituted metalloid wherein the metalloid is selected from Group 14 of the Periodic Table of the Elements, said R"", when a multi-atomic ligand group, containing up to 20 nonhydrogen atoms.

Preferably, R"" independently in each occurrence is selected from the group consisting of hydrogen, methyl, ethyl, and all isomers of propyl, butyl, pentyl and hexyl, as well as cyclopentyl, cyclohexyl, norbornyl, benzyl, and trimethylsilyl; or adjacent R"" groups are linked together thereby forming a fused ring system such as an indene-1-yl, 2-methylindene-1-yl, 3-methylindene-1-yl, 2,3-dimethylindene-1-yl, 2,3,5,6-tetramethylindene-1-yl, 2,3,5, 6,7,pentamethylindene-1-yl, 2-methyl-4-phenylindene-1-yl, 2-methyl-4-naphthylindene-1-yl, tetrahydroindene-1-yl, fluorene-1-yl, tetrahydrofluorene-1-yl, or octahydrofluorene-1-yl group.

Most preferred complexes according to formula III are those containing a divalent derivative of a cyclopentadienyl, indenyl, tetrahydroindenyl, fluorenyl, tetrahydrofluorenyl, or octahydrofluorenyl group, or one of the foregoing groups further substituted with one or more methyl, ethyl, propyl, butyl, pentyl, hexyl, (including branched and cyclic isomers), norbornyl, benzyl, or phenyl groups.

Examples of suitable X' moieties include: η$^4$-1,4-diphenyl-1,3-butadiene; η$^4$-1,3-pentadiene; η$^4$-1-phenyl-1, 3-pentadiene; η$^4$-1,4-dibenzyl-1,3-butadiene; η$^4$-2,4-hexadiene; η$^4$-3-methyl-1,3-pentadiene; η$^4$-1,4-ditolyl-1,3-butadiene; and η$^4$-1,4-bis(trimethylsilyl)-1,3-butadiene. Of the foregoing 1,4-diphenyl-1,3-butadiene, 1-phenyl-1,3-pentadiene, and 2,4 hexadiene are preferred.

Examples of suitable X" moieties include chloride, methyl, benzyl, phenyl, tolyl, t-butyl, methoxide, and trimethylsilyl or two X" groups together are 1,4-butanediyl, s-cis(1,3-butadiene), or s-cis(2,3-dimethyl-1,3-butadiene).

Preferred Z groups are those wherein E carbon and m is 2 or E is silicon and m is 1. Also preferably $R^2$ is methyl, phenyl, methoxide, ethoxide, propoxide or butoxide.

In the most preferred embodiment -Z-Y- is ($\eta^6$-1-phenylboratabenzene-4-yl)dimethylsilyl, ($\eta^6$-1-N,N-dimethylaminoboratabenzene-4-yl)dimethylsilyl, 1 ($\eta^6$-1-phenylboratabenzene-4-yl)ethane-2-yl, 1-($\eta^6$-1-N,N-dimethylaminoboratabenzene-4-yl)ethane-2-yl, ($\eta^6$-1-phenylboratabenzene-4-yl)phenylmethylsilyl, or ($\eta^6$-(1-N, N-dimethylamino)boratabenzene-4-yl)phenylmethylsilyl.

Illustrative derivatives of Group 3, 4 or Lanthanide metals of the foregoing formula that may be employed in the practice of the present invention include:

[($\eta^6$-1-phenylboratabenzene-4-yl)dimethyl($\eta^5$-tetramethylcyclopentadienyl)-silane]zirconium (II)1,4-diphenyl-1,3-butadiene,

[($\eta^6$-1-phenylboratabenzene-4-yl)dimethyl($\eta^5$-tetramethylcyclopentadienyl)-silane]titanium (II)1,3-pentadiene,

[($\eta^6$-1-phenylboratabenzene-4-yl)dimethyl($\eta^5$-tetramethylcyclopentadienyl)-silane]titanium (III) 2-(N,N-dimethylamino)benzyl,

[($\eta^6$-1-phenylboratabenzene-4-yl)dimethyl($\eta^5$-tetramethylcyclopentadienyl)-silane]zirconium (IV) dimethyl,

[1-($\eta^6$-1-phenylboratabenzene-4-yl)-2-($\eta^5$-tetramethylcyclopentadienyl)ethane]-zirconium (IV) dimethyl,

[1-($\eta^6$-1-methylboratabenzene-4-yl)-2-($\eta^5$-tetramethylcyclopentadienyl)ethane]-zirconium (IV) dimethyl,

[($\eta^6$-1-phenylboratabenzene-4-yl)dimethyl($\eta^5$-tetramethylcyclopentadienyl)-silane]zirconium (IV) dibenzyl,

[($\eta^6$-1-phenylboratabenzene-4-yl)dimethyl($\eta^5$-tetramethylcyclopentadienyl)-silane]zirconium (IV) dichloride,

[($\eta^6$-1-phenylboratabenzene-4-yl)dimethyl($\eta^5$-2-methylindenyl)silane]zirconium (II) 1,4-diphenyl-1,3-butadiene,

[($\eta^6$-1-phenylboratabenzene-4-yl)dimethyl($\eta^5$-methylindenyl)silane]zirconium (II) 1,3-pentadiene,

[($\eta^6$-1-phenylboratabenzene-4-yl)dimethyl($\eta^5$-2-methylindenyl)silanetitanium (III) 2-(N,N-dimethylamino)benzyl,

[($\eta^6$-1-phenylboratabenzene-4-yl)dimethyl($\eta^5$-2-methylindenyl)silane]hafnium (IV) dimethyl,

[($\eta^6$-1-phenylboratabenzene-4-yl)dimethy($\eta^5$-2-methylindenyl)silane]zirconium (IV) dibenzyl,

[($\eta^6$-1-methyl-2-phenylboratabenzene-4-yl)dimethyl($\eta^5$-2-methylindenyl)silane]-zirconium (IV) dibenzyl,

[1($\eta^6$-1-methyl-2-phenylboratabenzene-4-yl)-2-($\eta^5$-2-methylindenyl)ethane]zirconium (IV) dibenzyl,

[1 -($\eta^6$-1-methyl-2-phenylboratabenzene-4-yl)-2-($\eta^5$-2-methylindenyl)ethane]zirconium (IV) dimethyl,

[($\eta^6$-1-phenylboratabenzene-4-yl)dimethyl($\eta^5$-2-methylindenyl)silane]zirconium (IV) dichloride,

[($\eta^6$-1-phenylboratabenzene-4-yl)dimethyl($\eta^5$-3-methylindenyl)silane]zirconium (II) 1,4-diphenyl-1,3-butadiene,

[($\eta^6$-1-phenylboratabenzene-4-yl)dimethyl($\eta^5$-3-methylindenyl)silanetitanium (II)1,3-pentadiene,

[($\eta^6$-1-phenylboratabenzene-4-yl)dimethyl($\eta^5$-3-methylindenyl)siane]titanium (III) 2-(N,N-dimethylamino)benzyl,

[($\eta^6$-1-phenylboratabenzene-4-yl)dimethyl($\eta^5$-3-methylindenyl)silane]zirconium (IV) dimethyl,

[($\eta^6$-1-phenylboratabenzene-4-yl)dimethyl($\eta^5$-3-methylindenyl)silane]hafnium (IV) dibenzyl,

[($\eta^6$-1-phenylboratabenzene-4-yl)dimethyl($\eta^5$-3-methylindenyl)sitane]zirconium (IV) dichloride,

[($\eta^6$-1-phenylboratabenzene-4-yl)dimethyl($\eta^5$-2,3-dimethylindenyl)silane]zirconium (II) 1,4-diphenyl-1,3-butadiene,

[($\eta^6$-1-phenylboratabenzene-4-yl)dimethyl($\eta^5$-2,3-dimethylindenyl)silane]titanium (II) 1,3-pentadiene,

[($\eta^6$-1-phenylboratabenzene-4-yl)dimethyl($\eta^5$-2,3-dimethylindenyl)silane]titanium (III) S2-(N,N-dimethylamino)benzyl,

[($\eta^6$-1-phenylboratabenzene-4-yl)dimethyl($\eta^5$-2,3-dimethylindenyl)silane]zirconium (IV) dimethyl,

[($\eta^6$-1-](phenyl]boratabenzene-4-yl)dimethyl($\eta^5$-2,3-dimethylindenyl)silane]zirconium (IV) dibenzyl,

[1-($\eta^6$-1-methyl-2-(phenyl)boratabenzene-4-yl)-2-($\eta^5$-2,4-dimethylindenyl)ethane]zirconium (IV) dibenzyl,

[($\eta^6$-1-phenylboratabenzene-4-yl)dimethyl($\eta^5$-2,3-dimethylindenyl)silane]hafnium (IV) dichloride,

[($\eta^6$-1-phenylboratabenzene-4-yl)dimethyl($\eta^5$-2-methyl-4-phenylindenyl)-silane]zirconium (II)1,4-diphenyl-1,3-butadiene,

[($\eta^6$-1-methyl-2-phenylboratabenzene-4-yl)dimethyl($\eta^5$-2-methyl-4-phenylindenyl)-silane]zirconium (II)1,4-diphenyl-1,3-butadiene,

[1-($\eta^6$-1-methyl-2-phenylboratabenzene-4-yl)-2-($\eta^5$-2-methyl-4-phenylindenyl)-ethane]zirconium (IV)dimethyl

[($\eta^6$-1-phenylboratabenzene-4-yl)dimethyl($\eta^5$-2-methyl-4-phenylindenyl)silane]zirconium (II) 1,3-pentadiene,

[($\eta^6$-1-phenylboratabenzene-4-yl)dimethyl($\eta^5$-2-methyl-4-phenylindenyl)silane]titanium (III) 2-(N,N-dimethylamino)benzyl,

[($\eta^6$-1-phenylboratabenzene-4-yl)dimethyl($\eta^5$-2-methyl-4-phenylindenyl)silane]zirconium (IV) dimethyl,

[($\eta^6$-1-phenylboratabenzene-4-yl)dimethyl($\eta^5$-2-methyl-4-phenylindenyl)silane]zirconium (IV) dibenzyl,

[($\eta^6$-1-phenylboratabenzene-4-yl)dimethyl($\eta^5$-2-methyl-4-phenylindenyl)silane]zirconium (IV) dichloride,

[($\eta^6$-1-phenylboratabenzene-4-yl)dimethyl($\eta^5$-tetrahydrofluorenyl)silane]titanium (II) 1,4-diphenyl-1,3-butadiene,

[($\eta^6$-1-phenylboratabenzene-4-yl)dimethyl($\eta^5$-tetrahydrofluorenyl)silane]zirconium (II) 1,3-pentadiene,

[($\eta^6$-1-phenylboratabenzene-4-yl)dimethyl n-tetrahydrofluorenyl)silane titanium (III) 2-(N,N-dimethylamino)benzyl,

[($\eta^6$-1-phenylboratabenzene-4-yl)dimethyl($\eta^5$-tetrahydrofluorenyl)silane]zirconium (IV) dimethyl,

[($\eta^6$-1-phenylboratabenzene-4-y()dimethyl($\eta^5$-tetrahydrofluorenyl)silane]zirconium (IV) dibenzyl,

[($\eta^6$-1-phenylboratabenzene-4-yl)dimethyl($\eta^5$-tetrahydrofluorenyl)silane]hafnium (IV) dichloride,

[($\eta^6$-1-boratabenzene-4-yl)dimethyl(($\eta^5$-tetramethylcyclopentadienyl)silane]zirconium (II) 1,4-diphenyl-1,3-butadiene,

[($\eta^6$-1-boratabenzene-4-yl)dimethyl($\eta^5$-tetramethylcyclopentadienyl)silane]titanium (II) 1,3-pentadiene,

[($\eta^6$-1-boratabenzene-4-yl)dimethyl($\eta^5$-tetramethylcyclopentadienyl)silane]titanium (III) 2-(N,N-dimethylamino)benzyl,

[($\eta^6$-1-boratabenzene-4-yl)dimethyl($\eta^5$-tetramethylcyclopentadienyl)silane]zirconium (IV) dimethyl,

[-(η⁶-1-boratabenzene-4-yl)-2-(η⁵-tetramethylcyclopentadienyl)ethane]zirconium (IV) dimethyl,

[1-(η⁶-1-(methyl)boratabenzene-4-yl)-2-(η⁵-tetramethylcyclopentadienyl)-ethane]zirconium (IV) dimethyl,

[(η⁶-1-boratabenzene-4-yl)dimethyl(η⁵-tetramethylcyclopentadienyl)silane]zirconium (IV) dibenzyl,

[(η⁶-1-boratabenzene-4-yl)dimethyl(η⁵-tetramethylcyclopentadienyl)silane]zirconium (IV) dichloride,

[(η⁶-1-boratabenzene-4-yl)dimethyl(η⁵-2-methylindenyl)silane]zirconium (II)1,4-diphenyl-1,3-butadiene,

[(η⁶-1-(phenyl)boratabenzene-4-yl)dimethyl(η⁵-2-methylindenyl)silane]zirconium (II) 1,3-pentadiene,

[(η⁶-1-boratabenzene-4-yl)dimethyl(η⁵-2-methylindenyl)silane]titanium (III) 2-(N,N-dimethylamino)benzyl,

[(η⁶-1-boratabenzene-4-yl)dimethyl(η⁵-2-methylindenyl)silane]hafnium (IV) dimethyl, boratabenzene-4-yl)dimethyl(η⁵-2-methylindenyl)sitane]zirconium (IV) dibenzyl,

[(η⁶-1-methyl-2-(phenyl)boratabenzene-4-yl)dimethyl(η⁵-2-methylindenyl)silane]-zirconium (IV) dibenzyl,

[1-(η⁶-1-methyl-2-phenylboratabenzene-4-yl)-2-(η⁵-2-methylindenyl)ethane]zirconium (IV) dibenzyl,

[1(η⁶-1-methyl-2-phenylboratabenzene-4-yl)-2-(η⁵-2-methylindenyl)ethane]zirconium (IV) dimethyl,

[(η⁶-1-boratabenzene-4-yl)dimethyl(η⁵-2-methylindenyl)sitane]zirconium (IV) dichloride,

[(η⁶-1-boratabenzene-4-yl)dimethyl n-3-methylindenyl)silane]zirconium (II) 1,4-diphenyl-1,3-butadiene,

[(η⁶-1-boratabenzene-4-yl)dimethyl(η⁵-3-methylindenyl)silane]titanium (II) 1,3-pentadiene,

[(η⁶-1-boratabenzene-4-yl)dimethyl(η⁵-3-methylindenyl)silane]titanium (III) 2-(N,N-dimethylamino)benzyl,

[(η⁶-1-boratabenzene-4-yl)dimethyl(η⁵-3-methylindenyl)silane]zirconium (IV) dimethyl,

[(η⁶-1-boratabenzene-4-yl)dimethyl(η⁵-3-methylindenyl)silane]hafnium (IV) dibenzyl,

[(η⁶-1-boratabenzene-4-yl)dimethyl(η⁵-3-methylindenyl)silane]zirconium (IV) dichloride,

[(η⁶-1-boratabenzene-4-yl)dimethyl(η⁵-2,3-dimethylindenyl)silane]zirconium (II)1,4-diphenyl-1,3-butadiene,

[((η⁶-1-boratabenzene-4-yl)dimethyl(η⁵-2,3-dimethylindenyl)silane]titanium (II)1,3-pentadiene,

[(η⁶-1-boratabenzene-4-yl)dimethyl(η⁵-2,3-dimethylindenyl)silane]titanium (III) 2-(N,N-dimethylamino)benzyl, dimethyl,

[(η⁶-1-boratabenzene-4-yl)dimethyl(η⁵-2,3-dimethylindenyl)silane]zirconium (IV) dibenzyl,

[1-(η⁶-1-methyl-2-(phenyl)boratabenzene-4-yl)-2-(η⁵-2,4-dimethylindenyl)ethane]zirconium (IV) dibenzyl,

[(η⁶-1-boratabenzene-4-yl)dimethyl(η⁵-2,3-dimethylindenyl)silane]hafnium (IV) dichloride,

[(η⁶-1-boratabenzene-4-yl)dimethyl(η⁵-2-methyl-4-phenylindeny)silane]zirconium (II) 1,4-diphenyl-1,3-butadiene,

[(η⁶-1-methyl-2-phenylboratabenzene-4-yl)dimethyl(η⁵-methyl-4-phenylindenyl)-silane]zirconium (II)1,4-diphenyl-1,3-butadiene,

[1-(η⁶-1-methyl-2-(phenyl)boratabenzene-4-yl)-2-(η⁵-2-methyl-4-phenylindenyl)ethane]zirconium (IV)dimethyl

[(η⁶-1-boratabenzene-4-yl)dimethyl(η⁵-2-methyl-4-phenylindenyl)silane]zirconium (II) 1,3-pentadiene,

[(η⁶-1-boratabenzene-4-yl)dimethyl(η⁵-2-methyl-4-phenylindenyl)silane]titanium (III) 2-(N,N-dimethylamino)benzyl,

[(η⁶-1-boratabenzene-4-yl)dimethyl(η⁵-2-methyl-4-phenylindenyl)silane]zirconium (IV) dimethyl,

[(η⁶-1-boratabenzene-4-yl)dimethyl(η⁵-2-methyl-4-phenylindenyl)sitane]zirconium (IV) dibenzyl,

[((η⁶-1-boratabenzene-4-yl)dimethyl((η⁵-2-methyl-4-phenylindenyl)silane]zirconium (IV) dichloride,

[(η⁶-1-boratabenzene-4-yl)dimethyl(η⁵-tetrahydrofluorenyl)silane]titanium (II)1,4-diphenyl-1,3-butadiene,

[(η⁶-1-boratabenzene-4-yl)dimethyl η⁵-tetrahydrofluorenyl)silane]zirconium (II) 1,3-pentadiene,

[(η⁶-1-boratabenzene-4-yl)dimethyl(η⁵-tetrahydrofluorenyl)silane]titanium (III) 2-(N,N-dimethylamino)benzyl,

[(η⁶-1-boratabenzene-4-yl)dimethyl(η⁵-tetrahydrofluorenyl)silane]zirconium (IV) dimethyl,

[(η⁶-1-boratabenzene-4-yl)dimethyl(η⁵-tetrahydrofluorenyl)silane]zirconium (IV) dibenzyl,

[(η⁶-1-boratabenzene-4-yl)dimethyl(η⁵-tetrahydrofluorenyl)silane]hafnium (IV) dichloride,

[(η⁶-1-phenylboratabenzene-4-yl)dimethyl(η⁵-tetramethylcyclopentadienyl)-silane]zirconium (II)1,4-diphenyl-1,3-butadiene,

[(η⁶-1-phenylboratabenzene-4-yl)dimethyl(η⁵-tetramethylcyclopentadienyl)-silane]titanium (II)1,3-pentadiene,

[(η⁶-1-phenylboratabenzene-4-yl)dimethyl(η⁵-tetramethylcyclopentadienyl)-silane]titanium (II) 2-(N,N-dimethylamino)benzyl,

[(η⁶-1-phenylboratabenzene-4-yl)dimethyl(η⁵-tetramethylcyclopentadienyl)-silane]zirconium (IV) dimethyl,

[1(η⁶-1-phenylboratabenzene-4-yl)-2-(η⁵-tetramethylcyclopentadienyl)ethane]zirconium (IV) dimethyl,

[(η⁶-1-(methyl)boratabenzene-4-yl)-2-(η⁵-tetramethylcyclopentadienyl)ethane]zirconium (IV) dimethyl,

[(η⁶-1-phenylboratabenzene-4-yl)dimethyl(η⁵-tetramethylcyclopentadienyl)-silane]zirconium (IV) dibenzyl,

[(η⁶-1-phenylboratabenzene-4-yl)dimethyl(η⁵-tetramethylcyclopentadienyl)-silane]zirconium (IV) dichloride,

[(η⁶-1-N,N-diisopropylaminoboratabenzene-4-yl)dimethyl (η⁵-2-methylindenyl)silane]zirconium (II)1,4-diphenyl-1,3-butadiene,

[(η⁶-1-N,N-diisopropylaminoboratabenzene-4-yl)dimethyl (η⁵-2-methylindenyl)silane]zirconium (II) 1,3-pentadiene,

[(η⁶-1-N,N-diisopropylaminoboratabenzene-4-yl)dimethyl (η⁵-2-methylindenyl)silane]titanium (III) 2-(N,N-dimethylamino)benzyl,

[(η⁶-1-N,N-diisopropylaminoboratabenzene-4-yl)dimethyl (η⁵-2-methylindenyl)silane]hafnium (IV) dimethyl,

[(η⁶-1-N,N-diisopropylaminoboratabenzene-4-yl)dimethyl η⁵-2-methylindenyl)silane]zirconium (IV) dibenzyl,

[(η⁶-1-diisopropylamino-3-phenylboratabenzene-4-yl) dimethyl(η⁵-2-methylindenyl)silane]zirconium (IV) dibenzyl,

[1-(η⁶-1-diisopropylamino-2-phenylboratabenzene-4-yl)-2-(η⁵-2-methylindenyl)ethane]zirconium (IV) dibenzyl,

[1-(η⁶-1-diisopropylamino-2-phenylboratabenzene-4-yl)-2-(η⁵-2-methylindenyl)ethane]zirconium (IV) dimethyl,

[(η⁶-1-N,N-diisopropylaminoboratabenzene-4-yl)dimethyl (η⁵-2-methylindenyl)silane]zirconium (IV) dichloride,

[(η⁶-1-N,N-diisopropylaminoboratabenzene-4-yl)dimethyl (η⁵-3-methylindenyl)silane]zirconium (II)1,4-diphenyl-1,3-butadiene,

[(η⁶-1-N,N-diisopropylaminoboratabenzene-4-yl)dimethyl (η⁵-3-methylindenyl)silane]titanium (II) 1,3-pentadiene,

[(η⁶-1-N,N-diisopropylaminoboratabenzene-4-yl)dimethyl (η⁵-3-methylindenyl)silane]titanium (III) 2-(N,N-dimethylamino)benzyl,

[(η⁶-1-N,N-diisopropylaminoboratabenzene-4-yl)dimethyl (η⁵-3-methylindenyl)silane]zirconium (IV) dimethyl,

[(η⁶-1-N,N-diisopropylaminoboratabenzene-4-yl)dimethyl (η⁵-3-methylindenyl)silane]hafnium (IV) dibenzyl,

[(η⁶-1-N,N-diisopropylaminoboratabenzene-4-yl)dimethyl (η⁵-3-methylindenyl)silane]zirconium (IV) dichloride,

[(η⁶-1-N,N-diisopropylaminoboratabenzene-4-yl)dimethyl (η⁵-2,3-dimethylindenyl)silane]zirconium (I) 1,4-diphenyl-1,3-butadiene,

[(η⁶-1-N,N-diisopropylaminoboratabenzene-4-yl)dimethyl (η⁵-2,3-dimethylindenyl)silane]titanium (II) 1,3-pentadiene,

[(η⁶-1-N,N-diisopropylaminoboratabenzene-4-yl)dimethyl (η⁵-2,3-dimethylindenyl)-silane]titanium (III) 2-(N,N-dimethylamino)benzyl,

[(η⁶-1-N,N-diisopropylaminoboratabenzene-4-yl)dimethyl (η⁵-2,3-dimethylindenyl)silane]zirconium (IV) dimethyl,

[(η⁶-1-(N,N-diisopropylamino)boratabenzene-4-yl) dimethyl(η⁵-2,3-dimethylindenyl)silane]zirconium (IV) dibenzyl,

[1(η⁶-1-diisopropylamino-2-(phenyl)boratabenzene-4-yl)-2-(η⁵-2,4-dimethylindenyl)ethane]zirconium (IV) dibenzyl,

[(η⁶-1-N,N-diisopropylaminoboratabenzene-4-yl)dimethyl (η⁵-2,3-dimethylindenyl)silane]hafnium (IV) dichloride,

[(η⁶-1-N,N-diisopropylaminoboratabenzene-4-yl)dimethyl (η⁵-2-methyl-4-phenylindenyl)silane]zirconium (II)1,4-diphenyl-1,3-butadiene,

[(η⁶-1-diisopropylamino-2-phenylboratabenzene-4-yl) dimethyl(η⁵-2-methyl-4-phenylindenyl)silane]zirconium (II) 1,4-diphenyl-1,3-butadiene,

[1-(η⁶-1-diisopropylamino-2-phenylboratabenzene-4-yl)-2-(η⁵-2-methyl-4-phenylindenyl)ethane]zirconium (IV) dimethyl

[(η⁶-1-N,N-diisopropylaminoboratabenzene-4-yl)dimethyl (η⁵-2-methyl-4-phenylindenyl)silane]zirconium (II)1,3-pentadiene,

[(η⁶-1-N,N-diisopropylaminoboratabenzene-4-yl)dimethyl (η⁵-2-methyl-4-phenylindenyl)silane]titanium (III) 2-(N,N-dimethylamino)benzyl,

[(η⁶-1-N,N-diisopropylaminoboratabenzene-4-yl)dimethyl (η⁵-2-methyl-4-phenylindenyl)silane zirconium (IV) dimethyl,

[(η⁶-1-N,N-diisopropylaminoboratabenzene-4-yl)dimethyl (η⁵-2-methyl-4-phenylindenyl)silane]zirconium (IV) dibenzyl,

[(η⁶-1-N,N-diisopropylaminoboratabenzene-4-yl)dimethyl (η⁵-2-methyl-4-phenylindenyl)silane]zirconium (IV) dichloride,

[(η⁶-1-N,N-diisopropylaminoboratabenzene-4-yl)dimethyl η⁵-tetrahydrofluorenyl)-silane]titanium (II) 1,4-diphenyl-1,3-butadiene,

[(η⁶-1-N,N-diisopropylaminoboratabenzene-4-yl)dimethyl (η⁵-tetrahydrofluorenyl)-silane]zirconium (II)1,3-pentadiene,

[(η⁶-1-N,N-diisopropylaminoboratabenzene-4-yl)dimethyl (η⁵-tetrahydrofluorenyl)-silane]titanium (III) 2-(N,N-dimethylamino)benzyl,

[(η⁶-1-N,N-diisopropylaminoboratabenzene-4-yl)dimethyl η⁵-tetrahydrofluorenyl)-silane]zirconium (IV) dimethyl,

[(η⁶-1-N,N-diisopropylaminoboratabenzene-4-yl)dimethyl (η⁵-tetrahydrofluorenyl)-silane]zirconium (IV) dibenzyl, and

[(η⁶-1-N,N-diisopropylaminoboratabenzene-4-yl)dimethyl (η⁵-tetrahydrofluorenyl)-silane]hafnium (IV) dichloride.

Other metal complexes, especially compounds containing other Group 3, 4 or Lanthanide metals will, of course, be apparent to those skilled in the art. In addition other substituted boratabenzene ligands especially 1-benzyl, and 1-methyl substituted boratabenzenes will similarly be apparent to those skilled in the art.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum- modified methylalumoxane, or diisobutylalumoxane; strong Lewis acids, such as $C_{1-30}$ hydrocarbyl substituted Group 13 compounds, especially tri(hydrocarbyl)aluminum- or tri (hydrocarbyl)boron-compounds and halogenated derivatives thereof, having from 1 to 10 carbons in each hydrocarbyl or halogenated hydrocarbyl group, especially tris (pentafluorophenyl)borane; and nonpolymeric, inert, compatible, noncoordinating, ion forming compounds (including the use of such compounds under oxidizing conditions). A suitable activating technique is bulk electrolysis (explained in more detail hereinafter). Combinations of the foregoing activating cocatalysts and techniques may also be employed if desired. The foregoing activating cocatalysts and activating techniques have been previously taught with respect to different metal complexes in the following references: EP-A-277,003, U.S. Pat. No. 5,153,157, U.S. Pat. No. 5,064,802, EP-A-468,651, EP-A-520,732 and WO93/23412.

Suitable nonpolymeric, inert, compatible, noncoordinating, ion forming compounds useful as cocatalysts in one embodiment of the present invention comprise a cation which is a Bronsted acid capable of donating a proton, and a compatible, noncoordinating, anion, $A^-$. Preferred anions are those containing a single coordination complex comprising a charge-bearing metal or metalloid core which anion is capable of balancing the charge of the active catalyst species (the metal cation) which is formed when the two components are combined. Also, said anion can be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are well known and many, particularly such compounds containing a single boron atom in the anion portion, are available commercially.

Additional suitable anions include sterically shielded diboron anions corresponding to the formula:

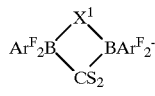

wherein:

S is alkyl, fluoroalkyl, aryl, or fluoroaryl (and where two S groups are present additionally hydrogen), $Ar^F$ is fluoroaryl, and $X^1$ is either hydrogen or halide.

Such diboron anions are disclosed in U.S. Pat. No. 5,447,895.

Preferably such cocatalysts may be represented by the following general formula:

$$(L^*-H)^+_d A^{d-}$$

wherein:

L* is a neutral ligand;

$(L^*-H)^+$ is a Bronsted acid;

$A^{d-}$ is a noncoordinating, compatible anion having a charge of d−, and d is an integer from 1 to 3.

More preferably d is one, that is, $A^{d-}$ is $A^-$.

Highly preferably, $A^-$ corresponds to the formula: $[BQ_4]^-$ wherein:

B is boron in the +3 formal oxidation state; and

Q independently each occurrence is selected from hydride, dialkylamino, halide, alkoxide, aryloxide, hydrocarbyl, halocarbyl, and halosubstituted-hydrocarbyl radicals, said Q having up to 20 carbons with the proviso that in not more than one occurrence is Q halide.

In a more highly preferred embodiment, Q is a fluorinated $C_{1-20}$ hydrocarbyl group, most preferably, a fluorinated aryl group, especially, pentafluorophenyl.

Illustrative, but not limiting, examples of ion forming compounds comprising proton donatable cations which may be used as activating cocatalysts in the preparation of the catalysts of this invention are tri-substituted ammonium salts such as:

trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl(2,4,6-trimethylanilinium) tetraphenylborate,
  trimethylammonium tetrakis-(penta-fluorophenyl) borate,
  triethylammonium tetrakis-(pentafluorophenyl) borate,
tripropylammonium tetrakis(pentafluorophenyl) borate, tri(n-butyl)-ammonium tetrakis(pentafluorophenyl) borate, tri(sec-butyl)ammonium tetrakis(pentafluorophenyl) borate, N,N-dimethylanilinium tetrakis (pentafluorophenyl) borate, N,N-diethylanilinium (pentafluoro-phenyl) borate, N,N-dimethyl(2,4,6-trimethyl-anilinium) tetrakis- (pentafluorophenyl) borate,
trimethylammonium tetrakis(2,3,4,6-tetrafluorophenylborate,
triethylammonium tetrakis(2,3,4,6-tetrafluorophenyl) borate,
tripropylammonium tetrakis(2,3,4,6-tetrafluorophenyl) borate,
tri(n-butyl)ammonium tetrakis(2,3,4,6-tetrafluorophenyl) borate,
dimethyl(t-butyl)ammonium tetrakis(2,3,4,6-tetrafluorophenyl) borate,
N,N-dimethylanilinium tetrakis(2,3,4,6-tetrafluorophenyl) borate,
N,N-diethylanilinium tetrakis(2,3,4,6-tetrafluorophenyl) borate, and
N,N-dimethyl-(2,4,6-trimethylanilinium) tetrakis-(2,3,4,6-tetrafluorophenyl) borate.

Dialkyl ammonium salts such as:
di-(i-propyl)ammonium tetrakis(pentafluorophenyl) borate, and dicyclohexylammonium tetrakis(pentafluorophenyl) borate.

Tri-substituted phosphonium salts such as: triphenylphosphonium tetrakis(pentafluorophenyl) borate, tri(o-tolyl) phosphonium tetrakis(penta-fluorophenyl) borate, and tri(2,6-dimethylphenyl)-phosphonium tetrakis(pentafluorophenyl) borate.

Preferred are N,N-dimethylanilinium tetrakis (pentafluorophenyl)borate and tributylammonium tetrakis (pentafluorophenyl)borate.

Another suitable ion forming, activating cocatalyst comprises a salt of a cationic oxidizing agent and a noncoordinating, compatible anion represented by the formula:

$$(Ox^{e+})_d(A^{d-})_e$$

wherein:

$Ox^{e+}$ is a cationic oxidizing agent having charge e+;

e is an integer from 1 to 3; and $A^{d-}$, and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis (pentafluorophenyl)borate.

Another suitable ion forming, activating cocatalyst comprises a compound which is a salt of a carbenium ion or silylium ion and a noncoordinating, compatible anion represented by the formula:

$$©^+A^-$$

wherein:

$©^+$ is a $C_{1-20}$ carbenium ion or silylium ion; and $A^-$ is as previously defined.

A preferred carbenium ion is the trityl cation, that is triphenylcarbenium. A preferred silylium ion is triphenylsilylium.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri (hydrocarbyl)aluminum compound having from 1 to 4 carbons in each hydrocarbyl group and a polymeric or oligomeric alumoxane.

An especially preferred activating cocatalyst comprises the combination of a trialkyl aluminum compound having from 1 to 4 carbons in each alkyl group and an ammonium salt of tetrakis(pentafluorophenyl)borate, in a molar ratio from 0.1:1 to 1:0.1, optionally up to 1000 mole percent of an alkylalumoxane with respect to M, is also present.

The activating technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), DME, and mixtures thereof.

The electrolysis may be conducted in a standard electrolytic cell containing an anode and cathode (also referred to as the working electrode and counter electrode respectively). Suitably materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally, an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, $A^-$. Preferred supporting electrolytes are salts corresponding to the formula:

$$G^+A^-;$$

wherein:

$G^+$ is a cation which is nonreactive towards the starting and resulting complex, and $A^-$ is a noncoordinating, compatible anion.

Examples of cations, $G^+$, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode.

Preferred supporting electrolytes are tetrahydrocarbylammonium salts of tetrakis(perfluoroaryl) borates having from 1 to 10 carbons in each hydrocarbyl group, especially tetra-n-butylammonium tetrakis(pentafluorophenyl) borate.

The molar ratio of catalyst/cocatalyst employed preferably ranges from 1:10,000 to 100:1, more preferably from 1:5000 to 10:1, most preferably from 1:10 to 1:2.

In general, the catalysts can be prepared by combining the two components (metal complex and activator) in a suitable solvent at a temperature within the range from −100° C. to 300° C. The catalyst may be separately prepared prior to use by combining the respective components or prepared in situ by combination in the presence of the monomers to be polymerized. It is preferred to form the catalyst in situ due to the exceptionally high catalytic effectiveness of catalysts prepared in this manner. The catalysts' components are sensitive to both moisture and oxygen and should be handled and transferred in an inert atmosphere.

As previously mentioned the present metal complexes are highly desirable for use in preparing supported catalysts. In this regard, the presence of the alkoxy functionality in the bridging group is particularly beneficial in allowing the complexes to chemically bind to hydroxyl, silane or chlorosilane functionality of the substrate materials. Especially suited substrates include alumina or silica. Suitable supported catalyst systems are readily prepared by contacting the present metal complexes with the substrate optionally while subjecting to heating and/or reduced pressures. A Lewis base, especially a trialkylamine can be present to assist in the reaction between the support and the alkoxy functionality of the metal complexes if desired.

Preferred supports for use in the present invention include highly porous silicas, aluminas, aluminosilicates, and mixtures thereof. The most preferred support material is silica. The support material may be in granular, agglomerated, pelletized, or any other physical form. Suitable materials include, but are not limited to, silicas available from Grace Davison (division of W. R. Grace & Co.) under the designations SD 3216.30, Davison Syloid 245, Davison 948 and Davison 952, and from Degussa AG under the designation Aerosil 812; and aluminas available from Akzo Chemicals Inc. under the designation Ketzen Grade B.

Supports suitable for the present invention preferably have a surface area as determined by nitrogen porosimetry using the B.E.T. method from 10 to 1000 $m^2/g$, and preferably from 100 to 600 $m^2/g$. The pore volume of the support, as determined by nitrogen adsorption, advantageously is between 0.1 and 3 $cm^3/g$, preferably from 0.2 to 2 $cm^3/g$. The average particle size is not critical, but typically s from 0.5 to 500 $\mu m$, preferably from 1 to 100 $\mu m$.

Both silica and alumina are known to inherently possess small quantities of hydroxyl functionality attached to the crystal structure. When used as a support herein, these materials are preferably subjected to a heat treatment and/or chemical treatment to reduce the hydroxyl content thereof. Typical heat treatments are carried out at a temperature from 30 to 1000° C. for a duration of 10 minutes to 50 hours in an inert atmosphere or under reduced pressure. Typical chemical treatments include contacting with Lewis acid alkylating agents such as trihydrocarbyl aluminum compounds, trihydrocarbylchlorosilane compounds, trihydrocarbylalkoxysilane compounds or similar agents. Preferred silica or alumina materials for use herein have a surface hydroxyl content that is less than 0.8 mmol hydroxyl groups per gram of solid support, more preferably less than 0.5 mmol per gram. The hydroxyl content may be determined by adding an excess of dialkyl magnesium to a slurry of the solid support and determining the amount of dialkyl magnesium remaining in solution via known techniques. This method is based on the reaction:

$$S-OH + Mg(Alk)_2 \rightarrow S-OMg(Alk) + (Alk)H,$$

wherein S is the solid support, and Alk is a $C_{1-4}$ alkyl group.

The support may be unfunctionalized (excepting for hydroxyl groups as previously disclosed) or functionalized by treating with a silane or chlorosilane functionalizing agent to attach thereto pendant silane —(Si—R)=, or chlorosilane —(Si—Cl)= functionality, wherein R is a $C_{1-10}$ hydrocarbyl group. Suitable functionalizing agents are compounds that react with surface hydroxyl groups of the support or react with the silicon or aluminum of the matrix. Examples of suitable functionalizing agents include phenylsilane, diphenylsilane, methylphenylsilane, dimethylsilane, diethylsilane, dichlorosilane, and dichlorodimethylsilane. Techniques for forming such functionalized silica or alumina compounds were previously disclosed in U.S. Pat. No. 3,687,920 and U.S. Pat. No. 3,879,368.

The support may also be treated with an aluminum component selected from an alumoxane or an aluminum compound of the formula $AlR^4_{x'} R^5_{y'}$, wherein $R^4$ independently each occurrence is hydride or $C_{1-20}$ hydrocarbyl, $R^5$ is hydride, $C_{1-10}$ hydrocarbyl or $C_{1-10}$ hydrocarbyloxy, x' is 2 or 3, y' is 0 or 1 and the sum of x' and y' is 3. Examples of suitable $R^4$ and $R^5$ groups include methyl, methoxy, ethyl, ethoxy, propyl (all isomers), propoxy (all isomers), butyl (all isomers), butoxy (all isomers), phenyl, phenoxy, benzyl, and benzyloxy. Preferably, the aluminum component is selected from the group consisting of aluminoxanes and tri($C_{1-4}$ hydrocarbyl)aluminum compounds. Most preferred aluminum components are aluminoxanes, trimethyl aluminum, triethyl aluminum, tri-isobutyl aluminum, and mixtures thereof.

Alumoxanes (also referred to as aluminoxanes) are oligomeric or polymeric aluminum oxy compounds containing chains of alternating aluminum and oxygen atoms, whereby the aluminum carries a substituent, preferably an alkyl group. The structure of alumoxane is believed to be represented by the following general formulae (—Al($R^6$)—O)$_{m'}$, for a cyclic alumoxane, and $R^6_2$Al—O(—Al($R^6$)—O)$_{m'}$—$AlR^6_2$, for a linear compound, wherein $R^6$ is $C_{1-10}$ alkyl, and m' is an integer ranging from 1 to 50, preferably at least 4. Alumoxanes are typically the reaction products of water and an aluminum alkyl, which in addition to an alkyl group may contain halide or alkoxide groups. Reacting several different aluminum alkyl compounds, such as for example trimethyl aluminum and tri-isobutyl aluminum, with water yields so-called modified or mixed alumoxanes. Preferred alumoxanes are methylalumoxane and methylalumoxane modified with minor amounts of $C_{2-4}$ alkyl groups, especially isobutyl. Alumoxanes generally contain minor to substantial amounts of starting aluminum alkyl compound.

Particular techniques for the preparation of alumoxane type compounds by contacting an aluminum alkyl compound with an inorganic salt containing water of crystallization are disclosed in U.S. Pat. No. 4,542,119. In a particular preferred embodiment an aluminum alkyl compound is contacted with a regeneratable water-containing substance such as hydrated alumina, silica or other substance. This is disclosed in EP-A-338,044. Thus the alumoxane may be incorporated into the support by reaction of a hydrated alumina or silica material, which has optionally been functionalized with silane, siloxane, hydrocarbyloxysilane, or chlorosilane groups, with a tri($C_{1-10}$ alkyl) aluminum compound according to known techniques.

The treatment of the support material in order to also include optional alumoxane or trialkylaluminum loadings involves contacting the same before, after or simultaneously with addition of the complex or activated catalyst hereunder with the alumoxane or trialkylaluminum compound, especially triethylaluminum or triisobutylaluminum. Optionally the mixture can also be heated under an inert atmosphere for a period and at a temperature sufficient to fix the alumoxane, trialkylaluminum compound, complex or catalyst system to the support. Optionally, the treated support component containing alumoxane or the trialkylaluminum compound may be subjected to one or more wash steps to remove alumoxane or trialkylaluminum not fixed to the support.

Besides contacting the support with alumoxane the alumoxane may be generated in situ by contacting an unhydrolyzed silica or alumina or a moistened silica or alumina with a trialkyl aluminum compound optionally in the presence of an inert diluent. Such a process is well known in the art, having been disclosed in EP-A-250,600, U.S. Pat. No. 4,912,075, and U.S. Pat. No. 5,008,228. Suitable aliphatic hydrocarbon diluents include pentane, isopentane, hexane, heptane, octane, isooctane, nonane, isononane, decane, cyclohexane, methylcyclohexane and combinations of two or more of such diluents. Suitable aromatic hydrocarbon diluents are benzene, toluene, xylene, and other alkyl or halogen substituted aromatic compounds. Most preferably, the diluent is an aromatic hydrocarbon, especially toluene. After preparation in the foregoing manner the residual hydroxyl content thereof is desirably reduced to a level less than 1.0 meq of OH per gram of support, by any of the previously disclosed techniques.

The catalysts, whether or not supported in any of the foregoing methods, may be used to polymerize ethylenically and/or acetylenically unsaturated monomers having from 2 to 100,000 carbon atoms either alone or in combination. Preferred monomers include the $C_{2-20}$ α-olefins especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, tetrafluoroethylene, vinylbenzocyclobutane, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

The catalysts of the invention are particularly adapted for use in the preparation of high molecular weight a-olefin homopolymers and copolymers, especially crystalline propylene homopolymers and copolymers having a high degree of isotacticity. In this regard the preferred catalysts are the corresponding racemic isomers of the metal complexes disclosed herein.

In general, the polymerization may be accomplished at conditions well known in the prior art for Ziegler-Natta or Kaminsky-Sinn type polymerization reactions, such as temperatures from 0–250° C. and pressures from atmospheric to 1000 atmospheres (0.1 to 100 MPa). Suspension, solution, slurry, gas phase or other process conditions may be employed if desired. The support, if present, is preferably employed in an amount to provide a weight ratio of catalyst (based on metal):support from 1:100,000 to 1:10, more preferably from 1:50,000 to 1:20, and most preferably from 1:10,000 to 1:30. Suitable gas phase reactions may utilize condensation of the monomer or monomers employed in the reaction, or of an inert diluent to remove heat from the reactor.

In most polymerization reactions the molar ratio of catalyst:polymerizable compounds employed is from $10^{-12}$:1 to $10^{-1}$:1, more preferably from $10^{-12}$:1 to $10^{-5}$:1.

Suitable solvents for polymerization via a solution process are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkyl-substituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-i-pentene, 4-methyl-1-pentene, 1,4-hexadiene, 1,7-octadiene, 1-octene, 1-decene, styrene, divinylbenzene, ethylidenenorbornene, allylbenzene, vinyltoluene (including all isomers alone or in admixture), 4-vinylcyclohexene, and vinylcyclohexane. Mixtures of the foregoing are also suitable.

The catalysts may also be utilized in combination with at least one additional homogeneous or heterogeneous polymerization catalyst in the same or in separate reactors connected in series or in parallel to prepare polymer blends having desirable properties. An example of such a process is disclosed in WO 94/00500. Alternatively, the two catalysts may be utilized in sequential or simultaneous polymerizations while being supported on a highly porous support or carrier, including a prepolymerized support that is capable of being permeated by an α-olefin.

Such polymerization process may comprise contacting, optionally in a solvent or in a nonsolvent, one or more α-olefins with a catalyst according to the present invention, in one or more continuous stirred tank or tubular reactors, or in the absence of solvent, optionally in one or more fluidized bed gas phase reactors, connected in series or parallel, and recovering the resulting polymer. Condensed monomer or solvent may be added to the gas phase reactor as is well known in the art. In the preparation of polypropylene the foregoing polymerization may further involve use of a porous inert carrier particle which optionally may be prepolymerized with polypropylene or other polymer.

In another process an ethylene /α-olefin interpolymer composition is prepared by:
  (A) contacting ethylene and at least one other a-olefin under polymerization conditions in the presence of a catalyst composition of the present invention in at least one reactor to produce a first interpolymer or optionally a solution of a first interpolymer,
  (B) contacting ethylene and at least one other a-olefin under polymerization conditions and at a higher polymerization reaction temperature than used in step (A) in the presence of a heterogeneous Ziegler catalyst in at least one other reactor to produce a second interpolymer optionally in solution, and
  (C) combining the first interpolymer and second interpolymer to form an ethylene/α-olefin interpolymer blend composition, and
  (D) recovering the ethylene/a-olefin interpolymer blend composition.

Preferably the heterogeneous Ziegler catalyst comprises:
  (i) a solid support component comprising magnesium halide, silica, modified silica, alumina, aluminum phosphate, or a mixture thereof, and
  (ii) a transition metal component represented by the formula:

$TrX'''_u(OR^6)_{v-u}$, $TrX'''_u R^6_{v-u}$, $VOX'''_3$ or $VO(OR^6)_3$, wherein:
  Tr is a Group 4, 5, or 6 metal,
  u is a number from 0 to 6 that is less than or equal to v,
  v is the formal oxidation number of Tr,
  X''' is halogen, and
  $R^6$ independently each occurrence is a $C_{1-10}$ alkyl group.

These polymerizations are generally carried out under solution conditions to facilitate the intimate mixing of the two polymer-containing streams. The foregoing technique allows for the preparation of ethylene/α-olefin interpolymer compositions having a broad range of molecular weight distribution and composition distribution. Preferably, the heterogeneous catalyst is also chosen from those catalysts which are capable of efficiently producing the polymers under high temperature, especially, temperatures greater than or equal to 180° C. under solution process conditions.

In a still further embodiment, there is provided a process for preparing polypropylene homopolymer or copolymer compositions, comprising:
  (A) polymerizing propylene and, optionally, at least one other α-olefin in a solution, slurry or gas phase process under suitable polymerization temperatures and pressures in at least one reactor containing a catalyst composition of the present invention, optionally supported on an inert support to produce a first polymer,
  (B) optionally passing the polymer of (A) into at least one other reactor in the presence of one other α-olefin under polymerization conditions to form a polypropylene/propylene/α-olefin interpolymer composition blend, and
  (C) recovering the resulting composition.

The foregoing technique also allows for the preparation of polypropylene and polypropylene/propylene/α-olefin interpolymer composition blends having a broad range of molecular weight distributions and composition distributions. Particularly desirable α-olefins for use in the foregoing processes are ethylene, C4-8 α-olefins, most desirably ethylene.

The skilled artisan will appreciate that the invention disclosed herein may be practiced in the absence of any component which has not been specifically disclosed.

EXAMPLE 1

[1,2-bis($n^6$-1-N, N-diisopropylaminoboratabenzene-4-yl)ethane]zirconium dichloride a) 1,2-Bis(1,1-dibutylstannacylohexa-2,5-dien-4-yl)ethane A solution of 1,1-dibutyl-1-stannacyclohexadienyllithium prepared from 1,1-dibutyl-1-stannacyclohexa-2,5-diene (0.08 g, 2.67 mmol) and 2.67 mmol of lithium diisopropylamide (LDA) in 20 mL of THF was added to a solution of 1,1-dibutyl-4-(2-bromoethyl)-1-stannacyclohexa-2,5-diene (1.0 g, 2.46 mmol) in 5 mL THF at −78° C. After stirring approximately 16 hours, 10 mL of water were added and the product was extracted with pentane, dried over $MgSO_4$, and evaporated to dryness. The red residue left contained 1.25 g (81 percent) of crude product.

$^1$H NMR ($C_6D_6$): δ0.9–1.5 (m, Bu), 1.62 (m,—$CH_2CH_2$), 3.11 (m, $H_\gamma$), 6.26 (dd, J=14.2, 1.5), 6.61 (dd, J=14.2, 4.3)
$^{13}$C NMR ($C_6D_6$): δ151.0 ($C_\beta$), 126.4 (Cα), 45.1 ($C_\gamma$), 33.7 ($CH_2CH_2$), 30.0, 27.8, 14.4, 11.4 (Bu)
HRMS (EI): calculated for $C_{24}H_{41}$ $^{120}Sn_2$ (M-Bu): 569.1252, found 569.1237 b) 1,2-Bis(1-chloro-1-boracyclohexa-2,5-dien-4-yl)ethane
A solution of 1,2-bis(1,1-dibutylstannacylohexa-2,5-dien-4-yl)ethane (1.25 g, 2.0 mmol) in pentane was added to a pentane solution of BCl₃ (1.0 g, 8.5 mmol) at −78° C. After stirring for two hours at room temperature, the solvent was removed and the product was extracted with pentane. The isolated product contained minor quantities of Bu₂SnCl₂.

H-NMR (C₆D₆): δ6.51 m (8H), δ2.34t, (H$_\gamma$) δ0.91 (m, CH₂CH₂)

C-NMR (C₆D₆): δ 161.4 (C$_\beta$), δ 133.9 (C$_\alpha$), δ 45.8 (C$_\gamma$), δ 28.3 (CH₂CH₂), B-NMR (C₆D₆) 51.7 c) 1,2-Bis(1-N,N-diisopropylamino-1-boracyclohexa-2,5-dien-4-yl)ethane 1,2-Bis(1-chloro-1-boracyclohexa-2,5-dien-4-yl)-ethane (1.5 g) was treated with excess diisopropylamine in pentane and left to stir for 2 hours. The solution was filtered and the filtrate was cooled at −20° C. Upon standing for several hours, solid formed which was separated from the filtrate. The filtrate was concentrated and left to stand at −20° C. for approximately 16 hours which caused the separation of more solid. The filtrate was separated and the pentane was removed under reduced pressure leaving an oily product containing small amounts of Bu₂SnCl₂ in addition to the desired product.

$^1$H NMR (C₆D₆): δ 6.73 (d, J=12.8), 6.55 (d, J=12.8), 3.69 (m, NCH), 2.82 (m, H$_\gamma$), 1.76 (m, CH₂CH₂), 1.12 (d. CH₃)

$^{13}$C NMR (C₆D₆): δ 151.2 (C$_\beta$), 131.3 (C$_\alpha$), 47.5 (NCH) 43.7 (C$_\gamma$), 31.6 (CH₂CH₂), 25.1 (CH₃)

HRMS (El): calculated for C₂₃H₃₉B₂N₂, 365.3299, found 365.3312 d) [1,2-Bis($\eta^6$-1-N,N-diisopropylaminoboratabenzene-4-yl)ethane]zirconium dichloride A solution of 1,2-bis(1-N,N-diisopropylamino-1-boracyclohexa-2,5-dien-4-yl)ethane (1.0 g, 2.7 mmol) in ether was treated with 2 equivalents of LDA in ether at −78° C. and left to stir for 2 hours at room temperature. The resulting suspension was transferred to an ether suspension of ZrCl₄ 0.63 g (2.7 mmol) at −78° C. The reaction was stirred at room temperature about 16 hours. Solvent removed and the residue was extracted with CH₂Cl₂ and treated with pentane and cooled at −20° C. for 24 hours. The crystals formed were collected and washed with pentane. The yield was 0.2 g (14 percent) based on the estimated purity of the starting material. Melting point=249° C.

$^1$H NMR (C₆D₆): δ 6.61 (d, J=11.4), 6.11 (d, J=11.4), 3.75 (m, CHN), 2.52 (s, CH₂CH₂), 1.31 (d. CH₃)

$^{13}$C NMR (C₆D₆): δ 138 (Cβ), 37.7, (CH₂CH₂), 47.1 (CHN), 23.9 (CH₃) $^{11}$B NMR ((C₆D₆): δ 30.0

HRMS (El): Calculated for C₂₃H₃₇B₂N₂Cl₂Zr: 523.1567, found 523.1581

EXAMPLE 2

(tert-butylamido)dimethyl($\eta^6$-1-N,N-diisopropylaminoboratabenzene-4-yl)silane]zirconium dichloride a) dimethylchloro(1-N,N-diisopropylamino-1-boracyclohexa-2,5-dien-4-yl)silane A solution of BuLi (2.5M in hexane, 3.6 ml, 6.98 mmol) was added dropwise with stirring to a solution of 1-(N,N-diisopropylamino)boracyclohexa-2,5-diene (prepared by reaction of 1,1-dibutyl-1-stannacyclohexadiene and BCl₃ followed by reaction with excess diisopropylamine at 20–25° C.) (1.22 g, 6.89 mmol) in THF (10 ml) at −78° C. The mixture was allowed to warm to 20–25° C. and stirred for 2 hours.

The mixture was slowly added to Me₂SiCl₂ (8.4 ml, 68.9 mmol) in a Shlenk vessel at −78° C. via cannula. After complete addition, the mixture was warmed to 20–25° C. and stirred for 2 hours. THF was removed under reduced pressure, pentane (5 ml) was added to assist THF removal. Pentane (20 ml) was added, the resulted white suspension was filtered through a sintered glass filter, and the solid was washed with pentane (10 ml). Pentane was removed under reduced pressure to afford product (1.81 g, 98 percent) as a yellowish oil:

$^1$H NMR (300 MHz, C₆D₆) δ 0.22 (s, 6H, SiCH₃),1.17 (d, 12H, J=6.9 Hz, NCHCH₃), 3.19 (tt, 1H, J=4.1, 1.0 Hz H(4)), 3.72 (m, 2H, NCH), 6.64 (dd, 2H, J=12.5, 1.0 Hz, H(2,6)), 6.95 (dd, 2H, J=12.5, 4.1 Hz, H(3,5))

$^{13}$C NMR (90 MHz, C₆D₆) δ-0.3 (SiCH₃), 23.7 (CH₃), 24.0 (CH₃), 44.8 (C(4)). 47.3 (NCH), 132.6 (br, C(2,6)), 144.7 (C(3,5))

$^{11}$ B NMR (115.5 MHz, C₆D₆) δ 31.2

MS(El) [m/e (intensity)]: 269 (10, M⁺), 254 (100), 212 (18)

MS(El) exact mass (m/z): calculated for C₁₃H₂₅BSiNCl, 269.1538; found 269.1535 b) (t-butylamino)dimethyl(1-N,N-diisopropylaminoboratabenzene-4-yl)silane

To a solution of dimethylchloro(1-N,N-diisopropylaminoboratabenzene-4-yl)silane (0.30 g, 1.11 mmol) in THF (10 ml) at −78° C. was added tert-butylamine (0.46 ml, 4.44 mmol). The mixture was allowed to warm to 20–25° C. and stirred for approximately 16 hours. THF was removed under reduced pressure, pentane (15 ml) was added, the resulting suspension was filtered through a sintered glass filter, the white solid was washed with pentane (5 ml). The filtrate was dried under reduced pressure to afford the product (0.34 g, 100 percent) as a yellowish oil.

$^1$H NMR (300 MHz, C₆D₆) δ 0.12 (s, 6H, SiCH₃),1.08 (s, 9H, C(CH₃)₃) 1.22 (d, 12H, J=6.9 Hz. NCHCH₃), 3.14 (t,1H, J=4.1 Hz, H(4)), 3.81 (m, 2H, NCH), 6.62 (d, 2H, J=12.4 Hz, H(2,6)), 7.07 (dd, 2H, J=12.4, 3.8 Hz, H(3.5))

$^{13}$C NMR (75 MHz, C₆D₆) δ 0.4 (SiCH₃), 24.0 (CH₃), 24.3 (CH₃), 34.4 (C(CH₃)₃), 46.7, 47.3, 49.4 (C(CH₃)₃), 130.3 (br, C(2,6)),148.0 (C(3,5))

$^{11}$B NMR (115.5 NHz, C₆D₆) δ 31.9

MS(Cl with NH₃) exact mass (m/z): calcd for C₁₇H₃₅BSiN₂H, 307.2741; found 307.2725 c) (tert-butylamido)dimethyl($\eta^6$-1-N,N-diisopropylaminoboratabenzene-4-yl)silane]zirconium dichloride To a solution of (t-butylamino)dimethyl(1-(N,N-diisopropylamino)boratabenzene-4-yl)silane(1.64 g, 5.36 mmol) in ether (20 ml) at −78° C. was added dropwise tBuLi (1.7M in pentane, 6.30 ml, 10.72 mmol). The mixture was warmed to 20–25° C. and stirred for 3 hours, a dark red solution was formed. The solution was added dropwise via cannula at −78° C. to a suspension of ZrCl₄ (1.28 g, 5.36 mmol) in either (10 ml). The mixture was gradually warmed to 20–25° C. and stirred about 16 hours. Ether was removed under reduced pressure, pentane (2×5 ml) was added to assist removal of ether. Residue was extracted with pentane (4×7 ml), and filtered through a sintered glass filter. The filtrate was concentrated to about 15 ml and cooled to −78° C. to give the crude product as a yellow solid. Recrystallization from pentane at −78° C. afforded the product (0.66 g, 26 percent) as yellow crystals: m.p.=200–200.5° C.

$^1$H NMR (360 MHz, C₆D₆) δ 0.26 (s, 6H, SiCH₃),1.21 (d, 6H, J=6.8 Hz, NCHCH₃),1.25 (d, 6H, J=6.8 Hz, NCHCH₃), 1.35 (s, 9H, C(CH₃)₃), 3.69 (m, 2H, NCH), 6.73 (d, 2H, J=11.2 Hz, H(2,6)), 7.08 (d, 2H, J=11.3 Hz, H(3,5))

$^{13}$C NMR (90 MHz, C$_6$D$_6$) δ 0.4 (SiCH$_3$), 22.8 (CH$_3$), 23.4 (CH$_3$), 33.3 (C(CH$_3$)$_3$), 47.2, 58.0, 95.7, 130.3 (br, C(2,6)), 144.4 (C(3,5))

$^{11}$B NMR (115.5 MHz, C$_6$D$_6$) δ 29.2

MS (Cl with Methane) [m/e (intensity)]: 465(4.0, M$^+$observed isotope pattern matches predicted), 451 (6.0), 450 (4.0)

MS (El) exact mass (m/z): calculated for C$_{16}$H$_{30}$BCl$_2$N$_2$SiZr ([M—CH$_3$]$^+$) 449.0695; found 449.0697

Elemental Analysis: calculated for C$_{17}$H$_{33}$BCl$_2$N$_2$SiZr: C, 43.68; H, 7.28; N, 6.00; found C. 44.00; H, 7.39; N, 5.64

EXAMPLE 3

[2-(η$^5$-cyclopentadienyl)-2-(η$^6$-1-N, N-diisopropylaminoboratabenzene-4-yl)prorane] zirconium dichloride a) 2-(Cyclopentadienyl)-2-(1-N,N-diisopropylaminoboratabenzene-4-yl)propane A solution of 6,6-dimethylfulvene (0.6 g, 5.7 mmol) in 5 mL of THF was added to (1-N,N-diisopropylaminoboratabenzene-4-yl)lithium, which had been prepared from 1-N,N-diisopropylamino-1-boracyclohexa-2,5-diene (1.0 g, 5.6 mmol) and BuLi (7.3 mmol), at −78° C. The reaction was allowed to warm to room temperature and stirred for 3 hours. To the resulting red solution was added 1 mL of water and the solvent was removed under reduced pressure. The residue was extracted with pentane and dried over MgSO$_4$, then the solvent was removed leaving an oily residue 1.0. g (62 percent yield) of crude product. The H-NMR indicated a mixture of isomers.

HRMS (El): calculated for C$_{19}$H$_{30}$BN: 283.2471, found 283.2468 b) [2-(η$^5$-Cyclopentadienyl)-2-(η$^6$-1-N,N-diisopropylaminoboratabenzene-4-yl)propane]zirconium dichloride A solution of the dilithium salt of 2-(cyclopentadienyl)-2-(1-N,N-diisopropylaminoboratabenzene-4-yl)propane (prepared from 0.8 g (2.8 mmol) of the ligand and 5.6 mmol of lithium diisopropylamide) in ether was added to 0.65 g (2.8 mmol) ZrCl$_4$ in ether at −78° C. The reaction mixture was stirred at 20–25° C. for about 16 hours. The solvent was removed under reduced pressure and the residue was washed with pentane. The remaining residue was extracted with toluene and treated with pentane. Upon standing about 16 hours in the freezer, microcrystalline product formed. The product was isolated and washed with pentane and dried. The yield is 0.3 g (24 percent). Mp, 234° C.

$^1$H NMR (C$_6$D$_6$): δ 6.71 (d, J=12.1), 6.51 (d, J=12.1) 6.3 (m, Cp), 5.0 (m, Cp), 3.88 (m, CHN), 1.12 (2, CMe$_2$), 1.12 (d, CHMe$_2$)

$^{13}$C NMR (C$_6$D$_6$): δ 133.2 (C$_β$), 124.1 (Cp), 104.2 (Cp), 60.4 (CMe$_2$), 47.0 (NCH), 30.5 (CHMe$_2$), 23.5 (CH$_3$); Cd not observed $^{11}$BNMR (CD$_6$): δ 27.3

HRMS (El):, Calculated for C$_{18}$H$_{25}$BCl$_2$NZr: 426.0504, found 426.0524

EXAMPLE 4

[bis(η$^6$-1-N, N-diisopropylaminoboratabenzene-4yl) dimethylsilane]-zirconium dichloride a) Bis(1-N,N-diisoproylaminoboratabenzene-4-yl) dimethylsilane To a solution of (1-N,N-diisoproylaminoboracyclohexa-2,5-diene (1.54 g, 8.70 mmol) in THF (15 ml) at −78° C. was added BuLi (2.5M hexane, 3.83 ml, 9.57 mmol). The mixture was allowed to warm to 20–25° C. and stirred for 2 hours. The resulting red solution was then added to a solution of (1-N,N-diisoproylaminoboratabenzene-4-yl) chlorodimethylsilane (2.27 g, 8.70 mmol) in THF (10 ml) at −78° C. The mixture was stirred about 16 hours at 20–25° C. Solvent was then removed and the residue was extracted with pentane (4×6 ml). Removal of pentane gave the desired product (4.63 g, 100 percent) as a yellow solid. A small portion of the product was recrystallized from pentane at −78° C. to give an analytically pure product. Melting point=100–102° C.

$^1$H NMR (300 NHz, CDCl$_3$) δ-0.13 (s, 6H, SiCH$_3$), 1.23 (d, 24H, J=6.9 Hz, NCHCH$_3$), 3.20 (t, 2H, J=4.1 Hz, H(4)), 3.79 (m, 2H, NCH), 6.42 (d, 4H, J=11.9 Hz, H(2,6)), 6.90 (dd, 2H, J=11.5, 6.2 Hz, H(3,5))

$^{13}$C NMR (75 MHz, CDCl$_3$) δ-6.6 (SiCH$_3$), 23.6 (CH$_3$), 24.0 (CH$_3$), 42.3, 46.9 130.3 (br, C(2,6)), 146.0 (C(3,5))

$^{11}$B NMR (115.5 MHz, (C$_6$D$_6$): δ 31.9

MS (El) exact mass (m/z): calculated for C$_{24}$H$_{44}$B$_2$N$_2$Si: 410.3460; found 410,3457

Elemental analysis, calculated for C$_{24}$H$_{44}$B$_2$N$_2$Si: C, 70.31; H, 10.74; N, 6.84, found C. 70.27; H, 10.92; N, 7.02 b) [Bis(η$^6$-1-N,N-diisopropylaminoboratabenzene-4-yl) dimethylsilane]zirconium dichloride To a solution of bis(1-N,N-diisoproylaminoboracyclohexa-2,5-dienyl)dimethylsilane (2.47 g, 5.85 mmol) in ether (17 ml) at −78° C. was added dropwise tBuLi (1.7M in pentane, 6.89 ml, 11.71 mmol). The mixture was warmed to 20–25° C. and stirred for 2 hours, during which time a dark red solution was formed. The solution was added dropwise via cannula at −78° C. to a suspension of ZrCl$_4$ (1.37 g, 5.90 mmol) in ether (10 ml). The mixture was gradually warmed to 20–25° C. and stirred about 16 hours. Ether was removed under reduced pressure and pentane (2×5 ml) was added to assist removal of ether. The residue was extracted with dichloromethane (3×8 ml) and filtered through a sintered glass filter. The filtrate was concentrated and recrystallized at −78° C. to give the desired product as a green solid. Melting point=152–153° C.

$^1$H NMR (300 MHz, CDCl$_3$) δ 0.73 (s, 6H, SiCH$_3$), 1.24 (d, 12H, J=6.8 Hz, NCHCH$_3$),1.25 (d, 12H, J=6.8 Hz, NCHCH$_3$), 3.75 (m, 4H, NCH), 6.35 (d, 4H, J=11.2 Hz, H(2,6)), 6.98 (d, 2H, J=1 1.2 Hz, H(3,5))

$^{13}$C NMR (90 MHz, CDCl$_3$- C$_6$D$_6$) δ-5.3 (SiCH$_3$), 23.5 (CH$_3$), 23.8 (CH$_3$), 46.7, 91.4 (C(4)),134.2 (br, C(2,6)), 139.3 (C(3,5))

$^{11}$B NMR (115.5 MHz, C$_6$D$_6$) δ 29.9

MS (El) exact mass (m/z), calculated for C$_{23}$H$_{39}$B$_2$Cl$_2$N$_2$SiZri ([M—CH$_3$]$^+$): 553,1493, found 553, 1497

Elemental analysis: calculated for C$_{24}$H$_{44}$B$_2$Cl$_2$N$_2$SiZrLiCl: C, 47.18; H, 6.88; N, 4.59, found C. 47.09; H, 6.92; N, 4.54, ([M—CH$_3$]$^+$) 449.0695, found 449.0697

Propylene polymerization

A two liter reactor is charged with mixed alkane solvent (Isopar-E™). Hydrogen is added by differential pressure expansion from a 75 ml addition tank from 300 psig (2.1 MPa) to near 275 psig (1.9 MPa). The reactor is then charged with 150 g of propylene monomer. The reactor and contents are then heated to and maintained at 70° C., the polymerization temperature. In an inert atmosphere glove box the appropriate quantities of metal complex and methyl alumoxane (MAO) cocatalyst solutions (0.00500M and 1.5M, respectively, in toluene) are combined and this catalyst solution is transferred to a catalyst addition tank. The polymerization is initiated by injecting this catalyst solution into the contents of the reactor. The polymerization conditions are maintained for the run time. Additional catalyst solution prepared and transferred in the same way may be added to the reactor throughout the course of the reaction. The polymer solution is removed from the reactor and combined with a hindered phenol antioxidant and isopropyl alcohol. Volatile components are removed from the polymer in a vacuum oven set at 140° C. for about 20 hours. The dried polymers are analyzed by $^{13}$C NMR spectroscopy and gel permeation chromatography (GPC). Results are contained in Table 1.

TABLE 1

| complex* (μmol) | MAO mmol | Isopar (g) | H$_2$ (Δ psi) | Run Time (min.) | yield (g) | Peak Molecular Weight | mmmm (%) | (mm)/(mr, m)/(rr) |
|---|---|---|---|---|---|---|---|---|
| Ex. 1 (18.0) | 18.0 | 652 | 26 | 70 | 1.6 | 158,900 | 22 | 34/35/31 |
| Ex. 3 (30.0) | 30.0 | 652 | 26 | 60 | 2.7 | 109,000 | small | 25/41/34 |
| Ex. 4 (15.0) | 15.0 | 655 | 25 | 44 | 3.0 | 800 | small | 23/43/37 |

*Ex. 1 = [1,2-bis(η$^6$-1-N,N-diisopropylaminoboratabenzene-4-yl)ethane]zirconium dichloride
Ex. 3 = [2-(η$^5$-cyclopentadienyl)-2-(η$^6$-1-N,N-diisopropylaminoboratabenzene-4-yl)propane] zirconium dichloride
Ex. 4 = [bis(η$^6$-1-N,N-diisopropylaminoboratabenzene-4yl)dimethylsilane]zirconium dichloride Ethylene/Octene copolymerization A two liter reactor is charged with mixed alkane solvent (Isopar-E) and 1-octene. Hydrogen is added by differential pressure expansion from a 75 ml addition tank from 300 psig (2.1 MPa) to near 275 psig (1.9 MPa). The reactor and contents are then heated to and maintained at 140° C., the polymerization temperature and saturated with ethylene at 500 psig (3.4 MPa). In an inert atmosphere glove box the appropriate quantities of metal complex and methyl alumoxane (MAO) cocatalyst solutions (0.00500M and 1.5M, respectively, in toluene) are combined and this catalyst solution transferred to a catalyst addition tank. The polymerization is initiated by injecting this catalyst solution into the contents of the reactor. The polymerization conditions are maintained for the run time with ethylene provided on demand at 500 psig (3.4 MPa). Additional catalyst solution prepared and transferred in the same way may be added to the reactor throughout the course of the reaction. The polymer solution is removed from the reactor and combined with a hindered phenol antioxidant and isopropyl alcohol. Volatile components are removed from the polymer in a vacuum oven set at 140° C. for about 20 hours. The dried polymers were analyzed by $^{13}$C NMR spectroscopy and GPC. Results are contained in Table 2.

What is claimed is:

1. A metal complex corresponding to the formula:

or a dimer, solvated adduct, chelated derivative or mixture thereof, wherein:

Y is a divalent derivative of a boratabenzene group or a hydrocarbyl-, dihydrocarbylamino-, silyl- or germyl- substituted boratabenzene group containing up to 50 nonhydrogen atoms that is bonded via its delocalized π-electrons to M;

L is a monovalent or divalent amido group, said L group containing up to 50 nonhydrogen atoms;

M is a metal of Group 3, 4 or the Lanthanide series of the Periodic Table of the Elements;

Z is a covalently bound, divalent substituent of up to 50 non-hydrogen atoms having the formula, —(ER$^2$$_2$)$_m$—, wherein E independently each occurrence is carbon, silicon or germanium, R$^2$ independently each occurrence is selected from the group consisting of hydrocarbyl, hydrocarbyloxy, silyl, and germyl of up to 20 atoms other than hydrogen, and m is an integer from 1 to 3;

X' is a neutral ligand having up to 20 non-hydrogen atoms;

X" independently each occurrence is a monovalent, anionic moiety selected from hydride, halo, hydrocarbyl, silyl, germyl, hydrocarbyloxy, amide, siloxy, halohydrocarbyl, halosilyl, silylhydrocarbyl, and dihydrocarbylaminohydrocarbyl having up to 20 non-hydrogen atoms, or two X" groups together form a divalent hydrocarbadiyl group;

TABLE 2

| complex* (μmol) | MAO mmol | Isopar (g) | 1-octene (g) | H$_2$ (Δ psi) | Run Time (min.) | yield (g) | Peak Molecular Weight | 1-octene (mole %) |
|---|---|---|---|---|---|---|---|---|
| Ex. 1 (12.0) | 12.0 | 747 | 120 | 26 | 48 | 26.1 | 15,700 | 1.0 |
| Ex. 2 (12.0) | 12.0 | 743 | 120 | 25 | 45 | 20.8 | 3,700 | 0.8 |
| Ex. 3 (3.0) | 3.0 | 743 | 123 | 26 | 30 | 26.2 | 83,900 | 0.7 |
| Ex. 4 (12.0) | 12.0 | 740 | 123 | 26 | 46 | 9.5 | 70,300 | 0.7 |

*Ex. 1 = [1,2-bis(η$^6$-1-N,N-diisopropylaminoboratabenzene-4-yl)ethane]zirconium dichloride
Ex. 2 = [(tert-butylamido)dimethyl(η$^6$-1-N,N-diisopropylaminoboratabenzene-4-yl)silane] zirconium dichloride
Ex. 3 = [2-(η$^5$-cyclopentadienyl)-2-(η$^6$-1-N,N-diisopropylaminoboratabenzene-4-yl)propane] zirconium dichloride
Ex. 4 = [bis(η$^6$-1-N,N-diisopropylaminoboratabenzene-4-yl)dimethylsilane]zirconium dichloride n is a number from 0 to 3; and p is an integer from 0 to 2 with the proviso that if L is Y or a hydrocarbadiyl group, then n is 1 and p is 0.

2. A metal complex corresponding to the formula:

wherein:

M is titanium, zirconium or hafnium in the +2 formal oxidation state;

Z is a covalently bound, divalent substituent of up to 50 non-hydrogen atoms having the formula, $-(ER^2{}_2)_m-$, wherein E independently each occurrence is carbon, silicon or germanium, $R^2$ independently each occurrence is selected from the group consisting of hydrocarbyl, hydrocarbyloxy, silyl, and germyl of up to 20 atoms other than hydrogen, and m is an integer from 1 to 3;

Y in each occurrence, independently is a divalent derivative of a boratabenzene group or a hydrocarbyl-, dihydrocarbylamino-, silyl- or germyl-substituted boratabenzene group containing up to 50 nonhydrogen atoms that is bonded via its delocalized π-electrons to M, and;

X' is a conjugated diene having from 4 to 30 non-hydrogen atoms, which forms a π-complex with M.

3. A metal complex according to claim 1 corresponding to the formula:

wherein:

M is titanium, zirconium or hafnium, in the +2, +3 or +4 formal oxidation state;

Z is a covalently bound, divalent substituent of up to 50 non-hydrogen atoms having the formula, $-(ER^2{}_2)_m-$, wherein E independently each occurrence is carbon, silicon or germanium, $R^2$ independently each occurrence is selected from the group consisting of hydrocarbyl, hydrocarbyloxy, silyl, and germyl of up to 20 atoms other than hydrogen, and m is an integer from 1 to 3;

Y is a divalent derivative of a boratabenzene group or a hydrocarbyl-, dihydrocarbylamino-,silyl- or germyl-substituted boratabenzene group containing up to 50 nonhydrogen atoms that is bonded via its delocalized π-electrons to M;

$R^1$ is $C_{1-20}$ hydrocarbyl,

X' is a conjugated diene having from 4 to 30 non-hydrogen atoms, which forms a π-complex with M when M is in the +2 formal oxidation state, whereupon n is 1 and p is 0; and X" each occurrence is an anionic ligand group that is covalently bonded to M when M is in the +3 or +4 formal oxidation state, whereupon n is 0 and p is 1 or 2, and optionally two X" groups together form a divalent anionic ligand group.

4. A metal complex according to claim 2 corresponding to the formula:

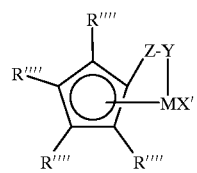

wherein:

M, Y, Z, and X' are as defined in claim 2; and

R"" is hydrogen, hydrocarbyl, silyl, halo-, cyano, dialkylamino, halohydrocarbyl, halocarbyl, dialkylamino substituted-hydrocarbyl, or hydrocarbyl-substituted metalloid wherein the metalloid is selected from Group 14 of the Periodic Table of the Elements, said R"", when a multi-atomic ligand group, containing up to 20 nonhydrogen atoms.

5. A metal complex according to claim 1 which is [(tert-butylamido)dimethyl($\eta^6$-1-N,N-diisopropylaminoboratabenzene-4-yl)silane]zirconium dichloride.

6. A catalyst composition comprising an activating cocatalyst and a metal complex according to any one of claims 1–4.

7. A supported catalyst composition comprising a catalyst composition according to claim 6 and a substrate.

8. A process for polymerizing an α-olefin, comprising contacting an α-olefin or a mixture of α-olefins with a catalyst composition according to claim 6.

9. A process for polymerizing an α-olefin, comprising contacting an α-olefin or a mixture of α-olefins with a catalyst system according to claim 7.

* * * * *

UNITED STATES PATENT AND TRADEMARK OFFICE
CERTIFICATE OF CORRECTION

PATENT NO. : 6,107,421
DATED : August 22, 2000
INVENTOR(S) : Francis J. Timmers, et al It is certified that error appears in the above-identified patent and that said Letters Patent is hereby corrected as shown below:

Claim 3, column 33,
Line 30, following "A metal complex" delete "according to claim 1".

Claim 4, column 34,
Line 14, following "A metal complex" delete "according to claim 2".

Claim 6, column 34,
Line 42, following "claims 1-4" insert -- or 11 --.

Signed and Sealed this

Ninth Day of October, 2001

Attest:

NICHOLAS P. GODICI
Attesting Officer
Acting Director of the United States Patent and Trademark Office